United States Patent [19]

Ito et al.

[11] Patent Number: 5,227,492

[45] Date of Patent: Jul. 13, 1993

[54] DIUREA DERIVATIVES USEFUL AS MEDICAMENTS AND PROCESSES FOR THE PREPARATION THEREOF

[75] Inventors: Noriki Ito, Saitama; Tomoyuki Yasunaga, Tokyo; Yuichi Iizumi, Chiba; Tomio Araki, Tokyo, all of Japan

[73] Assignee: Yamanouchi Pharmaceutical Co., Ltd., Tokyo, Japan

[21] Appl. No.: 906,735

[22] Filed: Jun. 30, 1992

Related U.S. Application Data

[60] Continuation of Ser. No. 764,617, Sep. 24, 1991, Pat. No. 5,166,429, which is a division of Ser. No. 592,604, Oct. 4, 1990, abandoned, which is a division of Ser. No. 296,443, Jan. 11, 1989, abandoned.

[51] Int. Cl.$^5$ ............................................. C07D 213/83
[52] U.S. Cl. .................................... 546/265; 546/308; 546/309; 564/27; 564/29; 564/50; 564/52; 564/53; 564/54; 564/55; 564/56; 564/57; 564/59
[58] Field of Search ................ 546/265, 308; 514/332, 514/352

[56] References Cited

U.S. PATENT DOCUMENTS

| | | | |
|---|---|---|---|
| 3,676,446 | 7/1972 | Schorr et al. | 546/265 |
| 4,216,228 | 8/1980 | Yamada et al. | 514/585 |
| 4,294,833 | 10/1981 | Innocenti et al. | 514/332 |
| 4,387,105 | 6/1983 | DeVries et al. | 514/595 |

FOREIGN PATENT DOCUMENTS

| | | | |
|---|---|---|---|
| 46-41462 | 12/1971 | Japan. | |
| 47-17899 | 5/1972 | Japan. | |
| 2048248 | 12/1980 | United Kingdom | 514/332 |
| 2080288 | 2/1982 | United Kingdom | 546/265 |

*Primary Examiner*—Richard L. Raymond
*Assistant Examiner*—Shailendra Kumar
*Attorney, Agent, or Firm*—Burgess, Ryan & Wayne

[57] ABSTRACT

Diurea derivatives are provided which can be represented by the following general formula and salts thereof:

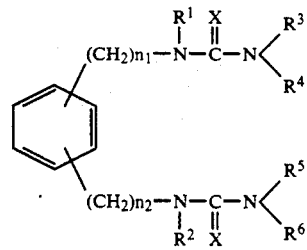

Illustrative derivatives include 1,3-bis[[1-cycloheptyl-3-(3-pyridyl)ureido]-methyl]benzene, 1,3-bis[[1-cycloheptyl-3-(2-pyridyl)ureido]-methyl]benzene, and 1,3-bis[[1-cycloheptyl-3-(4-pyridyl)ureido]-methyl]benzene.

The above compounds inhibit acyl-coenzyme A cholesterol acyltransferase (ACAT enzyme), and thereby control the accumulation of cholesterol ester to the smooth muscle of arterial wall in the blood vessel.

6 Claims, No Drawings

DIUREA DERIVATIVES USEFUL AS MEDICAMENTS AND PROCESSES FOR THE PREPARATION THEREOF

RELATED APPLICATIONS

This application is a continuation of application Ser. No. 764,617, filed Sep. 24, 1991, now U.S. Pat. No. 5,166,429, which in turn is a divisional application of Ser. No. 592,604, filed Oct. 4, 1990, now abandoned, which itself is a divisional application of Ser. No. 296,443, filed Jan. 11, 1989, now abandoned.

DETAILED DESCRIPTION OF INVENTION

1. Field of Industrial Application

The present invention relates to diurea derivatives represented by the following formula (I) useful as medicament and to processes for the preparation thereof;

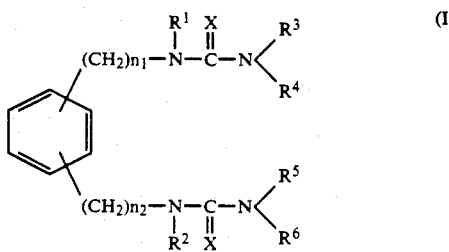

wherein, $R^1$ and $R^2$ are the same or different, and each represents an alkyl group, a cycloalkyl group, or a lower alkyl group substituted by cycloalkyl radical(s);

$R^3$, $R^4$, $R^5$ and $R^6$ are the same or different, and each represents a hydrogen atom, a lower alkyl group, a cycloalkyl group, an aralkyl group, a pyridyl group, or an unsubstituted or substituted phenyl group (the substituents of the phenyl group being selected from a group consisting of lower alkyl radical, halogen atom-substituted lower alkyl radical, halogen atom, nitro radical, amino radical, mono- or di-lower alkylamino radical, lower acylamino radical, hydroxyl radical, lower alkoxy radical and lower acyloxy radical), X represents an oxygen atom or a sulfur atom, and $n_1$ and $n_2$ represent an integer of 1 to 6.

Prior Art and Problems to be Solved by the Present Invention

It has been known that the deposition of cholesterol to the vascular system is an etiological cause of various diseases including coronary heart diseases. Among these, atheromatous arteriosclerosis is a form of arteriosclerosis which is characterized by the accumulation and hypertrophication of lipid, particularly cholesterol ester to the medium and large arterial wall.

Recently, it has been found that acyl-coenzyme A cholesterol acyl-transferase (ACAT) catalyzed the formation of cholesterol ester. Namely, the excessive accumulation of cholesterol ester to the arterial wall has connection with the increase of ACAT enzyme.

Accordingly, it is expected that by inhibiting the ACAT enzyme, the esterification speed of cholesterol may be descreased, and the formation and development of atheromatous disorder caused by the excessive accumulation of cholesterol ester to the arterial wall may be controlled.

On the other hand, cholesterols in foodstuffs are absorbed as a free cholesterol, esterified by the action of ACAT enzyme, and then released into the blood in the form of chylomicron. Therefore, it is expected that by inhibiting ACAT enzyme the absorption of cholesterols in foodstuffs into the intestine may be controoled and the re-absorption of cholesterol released into the intestine may be also controlled.

Means for solving the Problem

The inventors of the present invention have accomplished the present invention by preparing a compound which inhibits ACAT enzyme, and thereby prevents the deposition of cholesterol to the arterial wall and controls the absorption of cholesterol to the intestine.

Compounds disclosed in U.S. Pat. No. 4,387,105 have been known as ACAT enzyme inhibitor. However, the structure formula of compounds included in the present invention differs from that of compounds disclosed in said patent. In addition, although diruea compounds in which urea radical is connected to phenyl radical via alkylene are also disclosed in Japanese Patent Publication Nos. (Sho) 46-41462 and 47-29576, use of these compounds is described as stabilizing agent of polyolefines and anti-deteriorating agent for rubber. Furthermore, the structural formula of these compounds also differs from that of the present compound in view of the substituents of urea.

Accordingly, the present invention relates to diurea derivatives represented by formula (I) or salts thereof, and processes for the production thereof.

In the definitions of formula (I), "cycloalkyl" denotes cyclic alkyl having 3 to 18 carbon atoms, and examples thereof include cyclopropyl, cyclobutyl, cyclopentyl, cyclohexyl, cycloheptyl, cyclooctyl, cyclononyl, cyclodecyl, cyclododecyl, cyclotridecyl, cyclopentadecyl and the like. Particularly cycloalkyl having 6 to 10 carbon atoms is preferable.

"Lower alkyl" represents a straight or branched alkyl having 1 to 5 carbon atoms, and examples thereof include methyl, ethyl, propyl, isopropyl, butyl, isobutyl, sec.-butyl, tert.-butyl, pentyl (amyl), isopentyl, tert.-pentyl, neopentyl, 1-methylbutyl, 2-methylbutyl, 1,2-dimethylpropyl and the like. "lower alkyl substituted by cycloalkyl" means lower alkyl, any position of which is substituted by cycloalkyl, and examples thereof include cyclopropylmethyl, 2-cyclobutylethyl, cyclopentylmethyl, 2-cyclopentylethyl, 1-cyclopentylethyl, cyclohexylmethyl, 1-cyclohexylethyl, 2-cyclohexylethyl, 1-cyclohexylpropyl, 2-cyclohexylpropyl, 3-cyclohexylpropyl, 1-cyclohexylbutyl, 2-cyclohexylbutyl, 3-cyclohexylbutyl, 4-cyclohexylbutyl, cycloheptylmethyl, 2-cycloheptylethyl, 3-cycloheptylpropyl, 4-cycloheptylbutyl, 5-cycloheptylpentyl, cyclooctylmethyl, 2-cyclooxtylethyl, 3-cyclooctylpropyl, 4-cyclooctylbutyl, cyclononylmethyl, cyclodecylmethyl, cyclododecylmethyl, cyclotridecylmethyl, 2-cyclotridecylethyl, cyclo-tetradecylmethyl, cyclopentadecylmethyl and the like.

"Alkyl" represents alkyl having 1 to 10 carbon atoms, and in addition to the specific examples of said lower alkyl, examples thereof include a straight or branched alkyl such as hexyl, isohexyl, 1-methylpentyl, 2-methylpentyl, 3-methylpentyl, 1,1-dimethylbutyl, 1,2-dimethylbutyl, 1,3-dimethylbutyl, 2,2-dimethylbutyl, 2,3-dimethylbutyl, 1-ethylbutyl, 1,1,2-trimethylpropyl, 1-ethyl-1-methylpropyl, heptyl, 1-methylhexyl, 2-methylhexyl, 3-methylhexyl, 4-methylhexyl, 5-methylhexyl, 1,1-dimethylpentyl, 1,2-dimethylpentyl, 1,3-dimethylpentyl, 1,4-dimethylpentyl, 2,2-dimethylpentyl, 2,3-dimethylpentyl, 2,4-dimethylpentyl, 3,3-dimethylpentyl, 3,4-dimethylpentyl, 1-ethylpentyl, 2-ethylpentyl, 3-ethylpentyl, 1,1,2-trimethylbutyl, 1,1,3-trimethylbutyl, 1,2,2-trimethylbutyl, 2,2,3-trimethylbutyl, 1-ethyl-1-methylbutyl, 1-ethyl-2-methylbutyl, 1-ethyl-3-methylbutyl, 1-propylbutyl, 1-isopropylbutyl, octyl, 6-methylheptyl, nonyl, 7-methylocytl, decyl, 8-methylnonyl and the like.

"Aralkyl" represents an alkyl having 1 to 10 carbon atoms, which is substituted by aryl such as phenyl, naphtyl, pyridyl, and the like. Representative examples include benzyl, phenethyl, phenylpropyl, phenylbutyl, phenylpentyl, phenylhexyl, naphtylmethyl, pyridylmethyl, pyridylethyl and the like. "Pyridyl" include 2-, 3- or 4-prydidyl radicals.

In addition, phenyl radical may be unsubstituted or substituted by a lower alkyl radical, halogen atom-substituted lower alkyl radical, halogen atom, nitro radical, amino radical, mono- or di-lower alkylamino radical, lower acylamino radical, hydroxyl radical, lower alkoxy radical or lower acyloxy radical.

Lower alkyl as a substituent, has the above mentioned meanings. Halogen atom includes fluorine, chlorine, bromine and iodide. Lower alkyl substituted by halogen atom represents lower alkyl, any position of which is substituted by halogen, and examples thereof include trichloromethyl, trifluoromethyl, 2,2,2-trichloroethyl, 2,2,2-trifluoroethyl, 2,2,2-tribromoethyl and the like. Mono- or do-lower alkylamino represents amino substituted by one or two of said lower alkyl, and examples thereof include methylamino, ethylamino, propylamino, dimethylamino, diethylamino and the like. Lower acylamino represents amino substituted by acyl having 1 to 5 carbon atoms, and examples thereof include formylamino, acetylamino, propionylamino and butylylamino. Lower alkoxy includes methoxy, ethoxy, propoxy, isopropoxy, butoxy, isobutoxy, sec.-butoxy, tert.-butoxy, pentyloxy (amyloxy), isopentyloxy, tert.-pentyloxy, neopentyloxy, 2-methylbutoxy, 1,2-dimethylpropoxy, 1-ethylpropoxy and the like. Lower acyloxy represents acyloxy having 2 to 5 carbon atoms, and examples thereof include acetyloxy, propionyloxy, butylyloxy, and the like. The substituents of the phenyl may be substituted by the same or different one or more radicals.

The compound of formula (I) may form salts and the present invention also includes the salts of the compound of formula (I). Such salts include acid addition salts with mineral acids such as hydrochloric acid, hydrobromic acid, hydroiodic acid, sulfuric acid, nitric acid and phosphoric acid and the like, and with organic acids such as formic acid, acetic acid, oxalic acid, citric acid, succinic acid, fumaric acid, maleic acid, malic acid, tartaric acid, methanesulfonic acid, ethanesulfonic acid and the like.

Processes

The compound of formula (I) according to the present invention may be prepared by various methods.

Hereinafter, the representative methods are illustrated.

PROCESS VARIENT 1

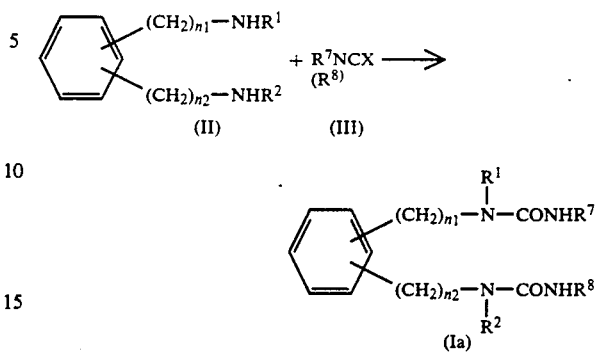

in the above formula
$R^7$ and $R^8$ are the same or different, and represent a hydrogen atom, a cycloalkyl group, an aralkyl group, a pyridyl group, or a phenyl group which may be substituted by lower alkyl, halogen, nitro, amino, mono- or di-lower alkylamino, lower acylamino, hydroxyl, lower alkoxy or lower acyloxy, and $R^1$, $R^2$, X, $n_1$ and $n_2$ have the above mentioned meanings.

Among the compounds of the present invention, compounds of formula ($I_a$) may be obtained by reacting diamino compound of formula (II) with one or two of isocyanate compound of formula (III). Isocyanate compound of formula (III) may be used in an amount of 2 mole to excessive moles per mole of the compound of formula (II).

The reaction may be carried out in an inert solvent, such as N,N-dimethylformamide, pyridine, benzene, toluene, dioxane, tetrahydrofuran, ether, chloroform, dichloromethane, dichloroethane, n-hexane and the like, at the room temperature or under heating.

PROCESS VARIANT 2

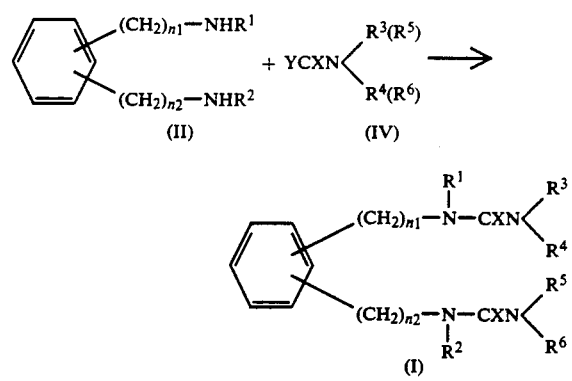

in the above formulae
Y represents a halogen atom, and $R^1$, $R^2$, $R^3$, $R^4$, $R^5$, $R^6$, X, $n_1$ and $n_2$ have the above mentioned meanings.

The compound of formula (I) of the present invention may be prepared by reacting amino compound of formula (II) with halogen compound of formula (IV). The reaction may be carried out by reacting amino compound of formula (II) with 2 moles to excessive moles of halogen compound of formula (IV) in an inert solvent, such as N,N-dimethylformamide, benzene, toluene, dioxane, tetrahydrofuran, ether, chloroform, dichloromethane, dichloroethane, n-hexane and the like. The reaction temperature may be suitably controlled according to the kind of starting compound and the solvent, but may be conventionally set at room temperature or under heating.

PROCESS VARIANT 3

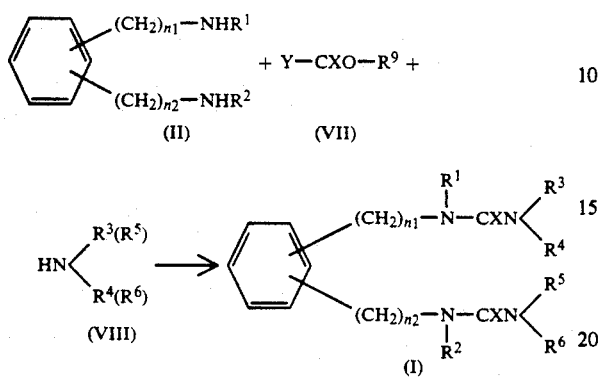

in the above formulae
$R^1$, $R^2$, $R^3$, $R^4$, $R^5$, $R^6$, X, Y, $n_1$ and $n_2$ have the above mentioned meanings, and
$R^9$ represents a lower alkyl group or a phenyl group.

The compound of formula (I) of the present invention may be obtained by reacting amino compound of formula (VIII) with carbon halide compound of formula (VII) to give carbamic acid ester, and then reacting the resulting compound with a compound of formula (II).

Examples of carbon halide compound represented by formula (VII) include isobutylcarbon chloride, methylcarbon chloride, ethylcarbon bromide, phenylcarbon chloride and the like. In addition, in order to promote the reaction, it is advantageous to effect the reaction in the presence of bases such as potassium carbonate, sodium carbonate, sodium hydroxyide, potassium hydroxide, triethylamine, N,N-dimethylanilline and the like. The reaction solvent includes inert solvents such as N,N-dimethylformamide, chloroform, benzene, toluene, xylene, dioxane, ether, tetrahydrofuran, chloroform, dichloromethane, dichloroethane and the like. When amino compound of formula (II) is reacted with carbon halide compound, the reaction temperature may be set under cooling or at the room temperature, whereas the reaction temperature in the case of the reaction between carbamic acid ester thus obtained and compound of formula (II) may be set at the room temperature or under heating.

As other methods for preparing the desired compound, a method for converting one of substituents in compound of formula (I) into other substituent may be mentioned. As a main mutual conversion, among the substituents of phenyl radical, a method for replacing an amino radical with mono- or di-alkylamino radical, a method for replacing nitro radical with amino radical, a method for replacing amino radical with acylamino radical, a method for replacing acyloxy radical with hydroxyl radical and the like may be mentioned.

Among these, in order to replace aromatic amino radical with aromatic (mono- or di-) alkylamino radical, although the conventional alkylation is employed, a reductive amination is preferable, in which the resulting compound is reacted with aldehyde to give imine, which is then reduced to amine.

For the reduction of imine, it is preferable to employ a catalyst such as palladium-carbon, platinium oxide and the like, or metal hydride such as sodium cyanoborohydride, lithium cyanoborohydride and the like.

For the replacement of aromatic nitro radical with aromatic amino redical, conventional catalytic reduction may be employed. Palladium-carbon, Raney-nickel, platinium and the like are used as catalysts.

In order to replace the aromatic amino radical with acylamino radical, conventional acylation, wherein active derivatives such as anhydride, halide, mixed acid anhydride of lower alkyl carboxylic acid are used, may be employed.

In addition, the substitution of the acyloxy radical for the hydroxy radical may be readily effected by using a base (for example, sodium hydroxide, potassium hydroxide, sodium carbonate and the like). Diamino compound of formula (II) which is used as a starting compound in the present invention may be prepared as follows:

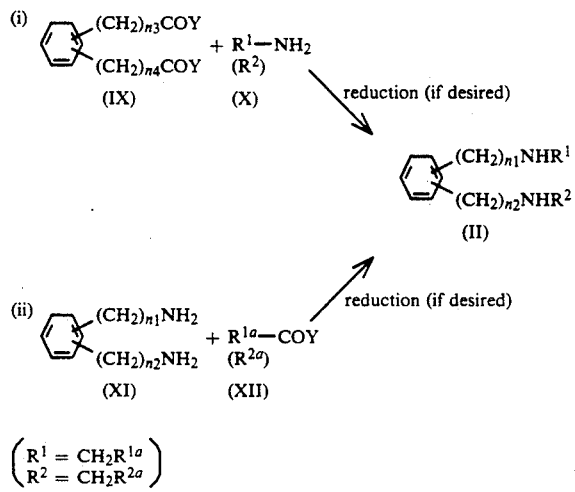

$$\begin{pmatrix} R^1 = CH_2R^{1a} \\ R^2 = CH_2R^{2a} \end{pmatrix}$$

in the above formulae
Y represents hydrogen atom or halogen atom,
$n_3$ and $n_4$ represent 0 or an integer of 1 to 5, and
$n_1$, $n_2$, $R^1$ and $R^2$ have the above mentioned meanings.

Phenylenediamine derivative having formula ($II_a$) may be obtained (i) by reacting carbonyl compound of formula (IX) with amino compound of formula (X) and then, if desired, reducing or (ii) by reacting diamine compound of formula (XI) with carbonyl compound of formula (XII) and then, if desired, reducing.

The reaction temperature between the compound of formula (IX) and the compound of formula (X), or between the compound of formula (XI) and the compound of formula (XII) may be set under ice-cooling or at the room temperature.

Benzene, hexane, toluene, xylene, dichloromethane, chloroform, N,N-dimethylformamide and the like are used as a reaction solvent. In addition, in order to accelerate the reaction, it is preferable to add an organic base such as trimethylamine, triethylamine and the like or an inorganic base such as sodium carbonate, sodium hydrogen carbonate and the like.

The reduction may be effected by using aluminium lithium hydride, diisobutylaluminium hydride, bis-(2-methoxyethoxy) aluminium sodium hydride, tetrahydrofurna-borate complex, dimethylsulfide-borate complex and the like, in a solvent such as toluene, benzene, xylene, tetrahydrofuran, dioxane, ether, etc. The reaction temperature may be conventionally set under ice-cooling or at the room temperature, heating. The compound of formula (I) or (II) of the present invention thus obtained may be separated and purified in free form or salt form by salt-forming or de-salting according to the conventional method; and extraction, crystallization, chromatography, etc.

Effects of the Invention

The compounds (I) of formula (I) of the present invention or salts thereof inhibit ACAT enzyme, and thereby control the accumulation of cholesterol ester to the smooth muscle of arterial wall in the blood vessel. In addition, as compared with known anti-lipidemia agents, the present compound controls the absorption of cholesterol to the intestine and accelerates catabolic escretion of cholesterol in liver, and thereby lowers the cholesterol level in blood. In addition, the present invention reduces the accumulation and storage of cholesterol at the arterial wall, and thereby controls the formation or developments of atheromatous arteriosclerosis.

Furthermore, as can be seen from animal test, compounds of formula (I) of the present invention or salts thereof have excellent action for lowering total cholesterol and low density lipoprotein (LDL) in blood. Therefore, the present compound exhibits and action for lowering lipid level in blood and is useful to prevent and treat the various diseases related to arteriosclerosis such as cerebral infarction, temporary ischemic spasm, angina pectrosis, peripheral thrombus and ileus.

Effects of the present compound may be verified by the following:

(i) ACAT enzyme inhibiting activity

EXPERIMENTAL EXAMPLE

Inhibiting activity against acyl CoA: cholesterol acyltranferase (ACAT) activity of rabbit's liver microsome According to Heider's method [J. G. Heider et al., J. of Lipid Res. Vol. 24, 1127-34 (1983)], rabbit's liver microsome was treated to obtain enzyme fraction.

To 0.154M of phosphoric acid buffer solution (pH 7.4), 2 mM of dithiothreitol, 36 μM of bovine serum albumin and 10 to 100 μg of microsome fraction, liposome prepared by Suckling's method [K. E. Suckling et al., FEBS Letters, Vol. 151, No. 1, 111-116 (1983)] was added to give 20% v/v. To this, 2% v/v of dimethylsolfoxide solution of each concentration of compound to be tested was added and the mixture was heated for 5 minutes at the temperature of 37° C. Then, 36 μM oleoyl CoA containing 1-$^{14}$C-oleoyl CoA was added and the whole mixture was heated for 10 minutes at the temperature of 37° C. The reaction was ceased by adding chloroform/methanol (=2/1). Upon stirring, cholesterol oleate extracted into chloroform layer was separated by thin layer chromatography and the radioactivity was then determined as ACAT activity.

TABLE 1

| Compound to be tested | Inhibiting activity against ACAT activity: IC (M) 50% |
| --- | --- |
| Compound of Example 1 | $1.8 \times 10^{-8}$ |
| Compound of Example 47 | $4.4 \times 10^{-8}$ |

(ii) Action for lowering lipid level in blood

To a male rat (5 weeks old) of Sprague-Dawley, bait containing 1.5% of cholesterol and 0.5% of bile acid was provided for 7 days, and for the last 5 days compound (I) of the present invention suspended in 0.5% aqueous solution of methylcellulose was orally administered via Sonde one time per day. After 2 hours from the last administration, blood was gathered under ehterization, and then the amount of total cholesterol in blood was determined according to Siedel's method [Siedel, J., et al., J. Clin. Chem. Clin. Biochem. 19, 838 (1981)] and the amount of HDL-cholesterol in blood was determined according to Ishikawa's method [Ischikawa, T.T., et al., Lipids 11, 628 (1976)]. According to these methods, the compound of formula (I) of the present invention or salts thereof effectively reduced cholesterol level in blood in 3 to 30 mg/kg.

Medicaments containing as a major component the compound of formula (I) of the present invention or salts thereof may be prepared by using pharmaceutical carriers and excipients used in the relevant art according to the conventional method.

The types of administration may include oral administration by tablets, pills, capsules, granules, dusts, solutions and the like, or parenteral administration by intravenous injection and intramuscular injections, suppositories and the like.

The dosage may be suitably determined depending upon the condition and age and sex of the subject and in the case of conventional oral administration the dosage is 50 to 500 mg per day for an adult in one or two to four doses.

EXAMPLES

The following examples illustrate the present invention in more detail. In the examples, $^1$H-NMR means hydrogen nuclear magnetic resonance spectrum, mp denotes melting point, Mass represents mass analysis value, and IR refers to infra red absorption spectrum.

Starting Material

Example (1)

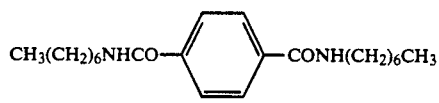

To a mixture of 4.6 g heptylamine, 4.04 g triethylamine and 30 ml methylene dichloride, was added with stirring 4.06 g terephthaloyl chloride under ice cooling. Stirring was continued at room temperature for two hours, and the solid which separated out was collected by filtration, washed with methylene dichloride and water in that order, and dried, giving 6.5 g of N,N'-diheptylterephthalamide.

(i) $^1$H-NMR (CDCl$_3$, δ ppm) 0.88 (6H, t), 3.28 (4H, q), 7.88 (4H, s)

(ii) Mass (EI) m/z 160 (M+)

The following compound was prepared in much the same manner as in Example(1).

Example (2)

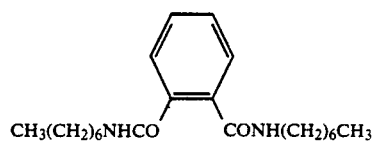

(i) $^1$H-NMR (CDCl$_3$, δ ppm) 0.90 (6H, t), 3.38 (4H, q), 7.52 (4H, m)
(ii) Mass (EI) m/z 360 (M$^+$)

Example (3)

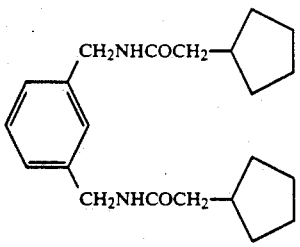

To a mixture of 1.36 g m-xylylenediamine, 2.4 g triethylamine and 50 ml methylene dichloride, was added with stirring 3.2 g cyclopentylacetyl chloride under ice cooling. Stirring was continued at room temperature for two hours, and the solid which separated out was collected by filtration, washed with methylene dichloride and water in that order and dried, giving 2 g of m-xylene-cyclopentylmethyldiamide.
(i) $^1$H-NMR (CDCl$_3$, δ ppm 4.40 (4, d), 6.84–7.44 (4H, m)
(ii) Mass (FAB) m/z 357 (M$^+$+1)

Example(4) (Starting material in Example 23)

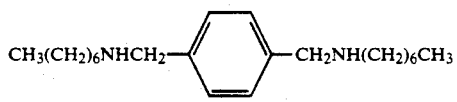

To a mixture of 3.6 g N,N'-diheptylterephthalamide obtained in Example 1 and 60 ml toluene, was added dropwise 15.6 ml of a 70% solution of bis(2-methoxyethoxy)aluminum hydride in toluene. After heating under reflux for three hours, the reaction mixture was treated with 30 ml of 2.5N aqueous caustic soda solution under ice cooling, and the toluene layer separated was washed with saturated aqueous solution of sodium chloride and dried over a drying agent. Distilling off the solvent from the dried solution gave 3.24 g of N,N'-diheptyl-p-xylylenediamine.
(i) $^1$H-NMR (CDCl$_3$, δ ppm) 0.88 (6H, t), 3.76 (4H, s), 7.26 (4H, s)
(ii) Mass (EI) m/z 332 (M$^+$)

The following two compounds were prepared in much the same manner as in Example 4.

Example (5)

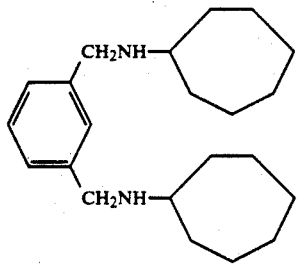

(i) $^1$H-NMR (CDCl$_3$, δ ppm) 3.74 (4H, s)
(ii) Mass (EI) m/z 328 (M$^+$)

Example (6) (Starting material in Example 21)

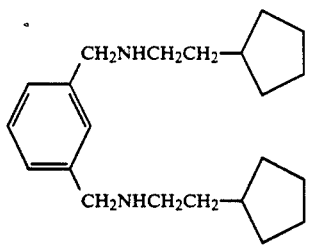

(i) $^1$H-NMR (CDCl$_3$, δ ppm) 2.64 (4H, t), 3.80 (4H, s)
(ii) Mass (FAB) m/z 329 (M$^+$+1)

Example (7)

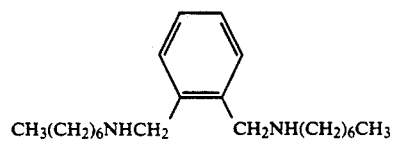

To a 1M solution of borane-tetrahydrofuran complex (24 ml) was added dropwise under ice cooling a 5 ml tetrahydrofuran solution containing 3.6 g of N,N'-diheptylphthalamide obtained in Example 2 under an argon gas stream, and the mixture was warmed up slowly and then heated under reflux for one hour. After cooling, 2 ml methanol was added dropwise under ice cooling, and the mixture was heated under reflux for 30 minutes. After cooling in ice, 4.24 ml concentrated hydrochloric acid was added, and the mixture was again heated under reflux for 30 minutes. The solvent was distilled off under reduced pressure, and the residue was basified by addition of an aqueous solution of caustic soda and extracted with chloroform. After distilling off the chloroform from the extract, the residue was purified by silica gel column chromatography, giving 0.43 g of N,N'-diheptyl-o-xylylenediamine.
(i) $^1$H-NMR (CDCl$_3$, δ ppm) 0.88 (6H, t), 2.64 (4H, t), 3.80 (4H, s)
(ii) Mass (CI) m/z 333 (M$^+$+1)

Example (8)

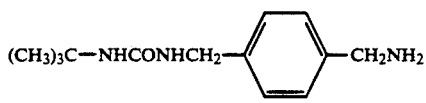

To a solution of 2.7 g p-xylylenediamine in 100 ml methylene dichloride, was added slowly with stirring 10 ml of a n-hexan solution containing 990 mg t-butyl isocyanate under ice cooling. Stirring was continued at room temperature for two hours, the solvent was distilled off under reduced pressure, and the residue was purified by silica gel column chromatography, giving 1 g of 4-(3-t-butylureidomethyl)-1-aminomethylbenzene.
(i) $^1$H-NMR (CDCl$_3$, δ ppm) 1.32 (9H, s), 3.84 (2H, s), 7.24 (4H, s)
(ii) Mass (EI) m/z 235 (M$^+$)

Example (9) (Starting material in Example 12)

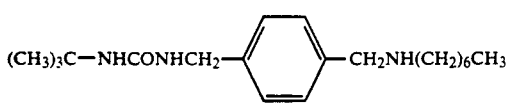

A mixture of 0.97 g 4-(3-t-butylureidomethyl)-1-aminomethylbenzene obtained in Example 8, 0.57 g anhydrous potassium carbonate and 20 ml dimethylformamide was stirred at room temperature for 30 minutes, 0.93 g 1-iodoheptane was added, and stirring was continued at room temperature for an additional three hours. After distilling off the solvent under reduced pressure, the residue was extracted with chloroform, and the extract was washed with water. The chloroform was distilled off under reduced pressure, and the residue was purified by silica gel column chromatography, giving 0.65 g g of 4-(3-t-butylureidomethyl)-1-(N-heptylaminomethyl)benzene.

(i) $^1$H-NMR (CDCl$_3$, δ ppm) 0.88 (3H, t), 2.60 (2H, t), 3.72 (2H, s)

(ii) Mass (EI) m/z 333 (M$^+$)

Example 1

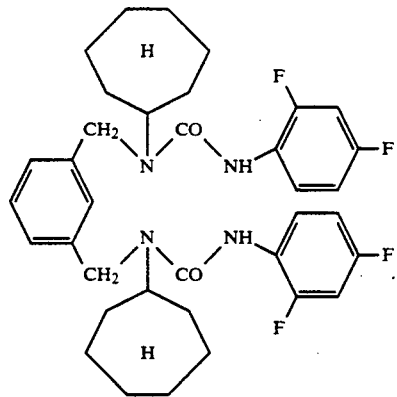

To a solution of 1 g N,N'-dicycloheptyl-m-xylylenediamine in 50 ml n-hexane, was added dropwise with stirring 5 ml of a n-hexane solution containing 1 g 2,4-difluorophenyl isocyanate under ice cooling. Stirring was continued at room temperature for two hours, the solvent was distilled off under reduced pressure, and the residue was purified by silica gel column chromatography and then recrystallized from isopropanol, giving 1.6 g of 1,3-bis[[1-cycloheptyl-3-(2,4-difluorophenyl)ureido]methyl]benzene.

(i) M.p. 71°–72° C.

(ii) Mass (FAB) m/z 639 (M$^+$ + 1)

| (iii) Elemental analysis (C$_{36}$H$_{42}$N$_4$O$_2$F$_4$) | | | |
|---|---|---|---|
| | C | H | N |
| Calcd. (%) | 67.69 | 6.63 | 8.77 |
| Found (%) | 67.68 | 6.71 | 8.74 |

The following four compounds were prepared in much the same manner as in Example 1.

Example 2

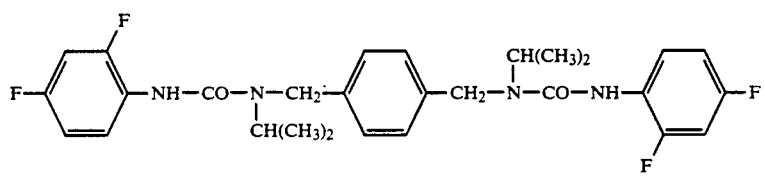

1,4-Bis[[3-(2,4-difluorophenyl)-1-isopropylureido]-methyl]benzene (i) M.p. 167°–168° C.

(ii) Mass (FAB) m/z 531 (M$^+$ + 1)

| (iii) Elemental analysis (C$_{23}$H$_{30}$N$_4$O$_2$F$_4$) | | | |
|---|---|---|---|
| | C | H | N |
| Calcd. (%) | 66.39 | 5.70 | 10.56 |
| Found (%) | 63.40 | 5.93 | 10.42 |

Example 2'

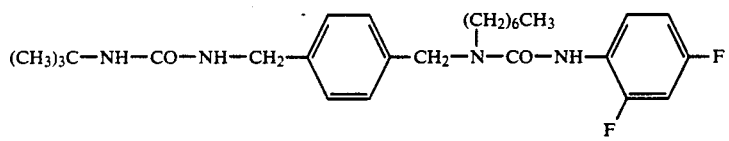

1-[p-(3-t-Butylureidomethyl)benzyl]-3-(2,4-difluoro-phenyl)-1-heptylurea (i) M.p. 117°–119° C.

(ii) Mass (EI) m/z 489 (M$^+$ + 1)

| (iii) Elemental analysis (C$_{27}$H$_{38}$N$_4$O$_2$F$_2$) | | | |
|---|---|---|---|
| | C | H | N |
| Calcd. (%) | 66.37 | 7.84 | 11.47 |
| Found (%) | 66.40 | 7.81 | 11.45 |

Example 3

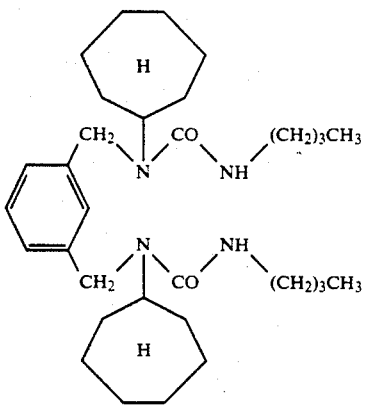

1,3-Bis[(3-butyl-1-cycloheptylureido)methyl]benzene (i) M.p. 132°–133° C.
(ii) Mass (FAB) m/z 527 (M$^+$+1)

| (iii) Elemental analysis ($C_{32}H_{54}N_4O_2$) | | | |
|---|---|---|---|
| | C | H | N |
| Calcd. (%) | 72.96 | 10.33 | 10.64 |
| Found (%) | 72.72 | 10.24 | 10.44 |

Example 4

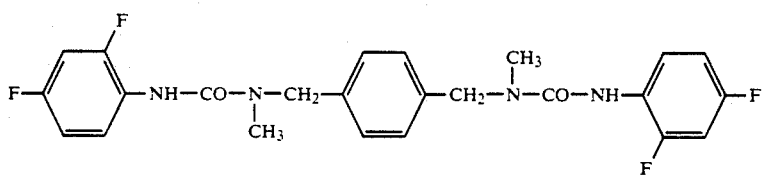

1,4-Bis[[3-(2,4-difluorophenyl)-1-methylureido]-methyl]benzene (i) M.p. 196°–198° C.
(ii) Mass (FAB) m/z 475 (M$^+$+1)

| (iii) Elemental analysis ($C_{24}H_{22}N_4O_2F_4$) | | | |
|---|---|---|---|
| | C | H | N |
| Calcd. (%) | 60.76 | 4.67 | 11.81 |
| Found (%) | 60.81 | 4.82 | 11.61 |

Example 5

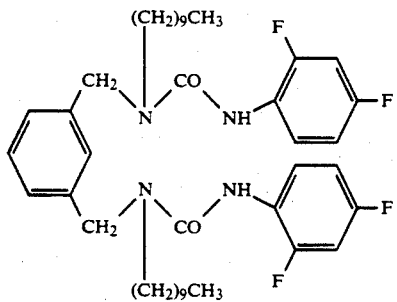

To a solution of 833 mg N,N'-didecyl-m-xylylenediamine in 20 ml n-hexane, was added dropwise with stirring 5 ml of a n-hexane solution containing 620 mg 2,4-difluorophenyl isocyanate under ice cooling. Stirring was continued at room temperature for two hours, the solvent was distilled off under reduced pressure, and the residue was purified by silica gel column chromatography, giving 750 mg of 1,3-bis[[1-decyl-3-(2,4-difluorophenyl)ureido]methyl]benzene.

(i) $^1$H-NMR (CDCl$_3$, δ ppm) 0.88 (6H, t), 3.36 (4H, t), 4.60 (4H, s)
(ii) IR (cm$^{-1}$), 1660, 1540, 1440

The following seven compounds were prepared in much the same manner as in Example 5.

Example 6

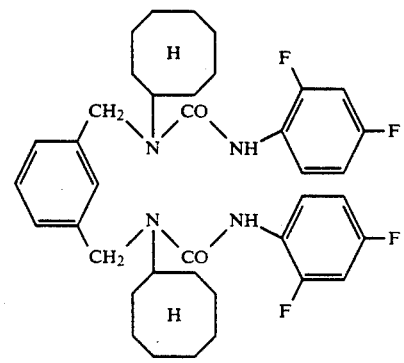

1,3-Bis[[1-cyclooctyl-3-(2,4-difluorophenyl)ureido]-methyl]benzene (i) $^1$H-NMR (CDCl$_3$, δ ppm) 4.48 (4H, s), 6.24 (1H, d), 8.02 (1H, m)
(ii) Mass (FAB) m/z 667 (M$^+$+1)
(iii) IR (cm$^{-1}$), 1672, 1536, 1432, 1198

Example 7

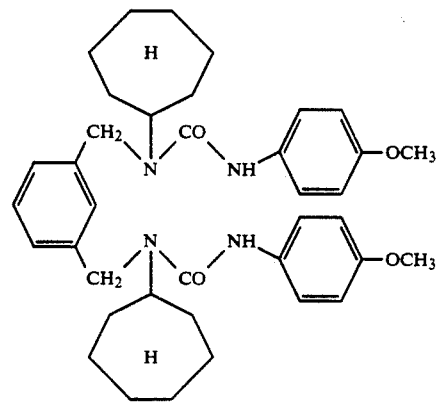

1,3-Bis[[1-cycloheptyl-3-(p-methoxyphenyl)ureido]-methyl]benzene (i) $^1$H-NMR (CDCl$_3$, δ ppm) 3.74 (6H, s), 4.52 (4H, s), 6.68 (4H, d)
(ii) Mass (FAB) m/z 627 (M$^+$ +1)
(iii) IR (cm$^{-1}$), 1646, 1514, 1232

Example 8

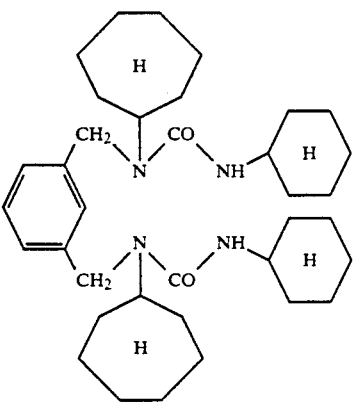

1,3-Bis[(1-cycloheptyl-3-cyclohexylureido)methyl]benzene (i) $^1$H-NMR (CDCl$_3$, δ ppm) 4.32 (4H, s)
(ii) Mass (FAB) m/z 579 (M$^+$ +1)
(iii) IR (cm$^{-1}$), 2860, 1636, 1530

Example 9

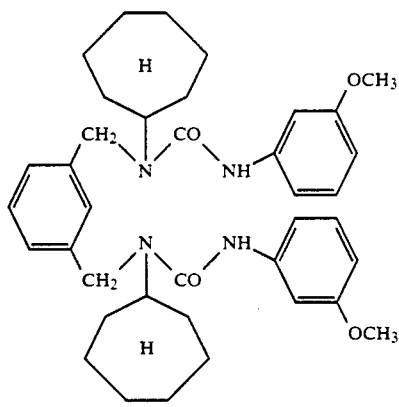

1,3-Bis[[1-cycloheptyl-3-(m-methoxyphenyl)ureido]-methyl]benzene (i) $^1$H-NMR (CDCl$_3$, δ ppm) 3.76 (6H, s), 4.48 (4H, s)
(ii) Mass (FAB) m/z 627 (M$^+$ +1)
(iii) IR (cm$^{-1}$), 1654, 1608, 1540, 1496, 1456

Example 10

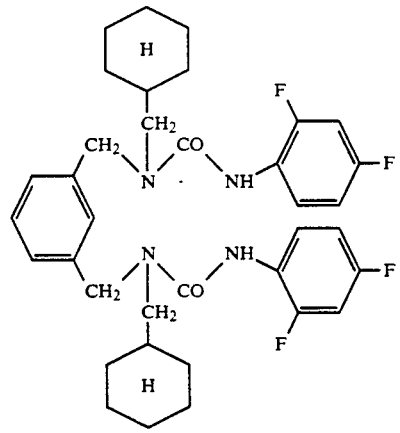

1,3-Bis[[3-(2,4-difluorophenyl)-1-cyclohexylmethylureido]methyl]benzene (i) $^1$H-NMR (CDCl$_3$, δ ppm) 3.18 (4H, d), 3.58 (4H, s), 6.42 (1H, d)
(ii) Mass (FAB) m/z 639 (M$^+$ +1)
(iii) IR (cm$^{-1}$), 2936, 1654, 1616, 1524

Example 11

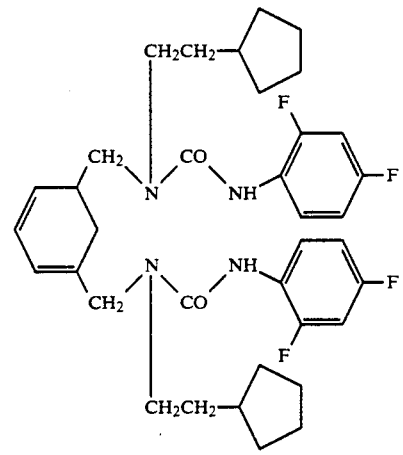

1,3-Bis[[3-(2,4-difluorophenyl)-1-cyclopentylethyl-ureido]methyl]benzene (i) $^1$H-NMR (CDCl$_3$, δ ppm) 3.36 (4H, t), 4.60 (4H, s), 6.42 (1H, d)
(ii) Mass (FAB) m/z 439 (M$^+$ +1)
(iii) IR (cm$^{-1}$), 2960, 1652, 1616, 1532, 1434

Example 12

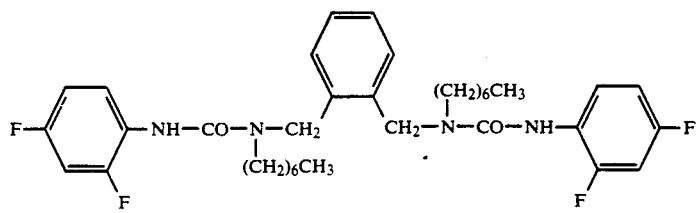

-continued 1,2-Bis[[3-(2,4-difluorophenyl)-1-heptylureido]-methyl]benzene (i) $^1$H-NMR (CDCl$_3$, δ ppm) 0.88 (6H, t), 3.36 (4H, t), 4.68 (4H, s)
(ii) Mass (FAB) m/z 643 (M$^+$+1)

Example 13

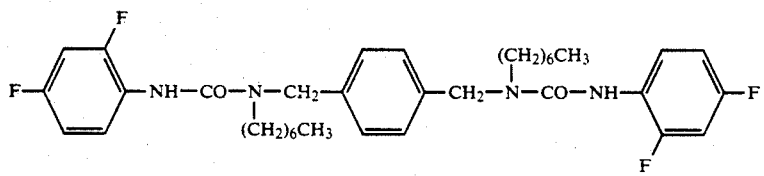

To a solution of 1.5 g N,N'-diheptyl-p-xylylenediamine in 20 ml n-hexane, was added dropwise with stirring 5 ml of a n-hexane solution containing 1.4 g 2,4-difluorophenyl isocyanate under ice cooling. Stirring was continued at room temperature for two hours, and the solid which separated out was collected by filtration and recrystallized from methanol, giving 2.3 g of 1,4-bis[[1-heptyl-3-(2,4-difluorophenyl)ureido]methyl]benzene.
(i) M.p. 107°–108° C.
(ii) Mass (EI) m/z 642 (M$^+$)

| (iii) Elemental analysis (C$_{36}$H$_{46}$N$_4$O$_2$F$_4$) | | | |
|---|---|---|---|
| | C | H | N |
| Calcd. (%) | 67.27 | 7.21 | 8.72 |
| Found (%) | 67.23 | 7.25 | 8.71 |

The following twelve compounds were prepared in much the same manner as in Example 23.

Example 14

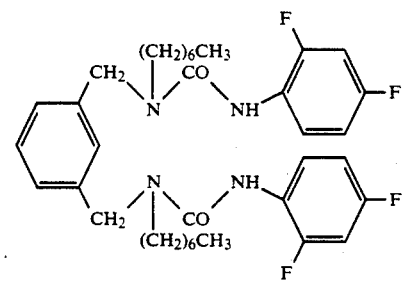

1,3-Bis[[3-(2,4-difluorophenyl)-1-heptylureido]-methyl]benzene (i) M.p. 69°–70° C.
(ii) Mass (FAB) m/z 643 (M$^+$+1)

| (iii) Elemental analysis (C$_{36}$H$_{46}$N$_4$O$_2$F$_4$) | | | |
|---|---|---|---|
| | C | H | N |
| Calcd. (%) | 67.27 | 7.21 | 8.72 |
| Found (%) | 67.23 | 7.33 | 8.70 |

Example 15

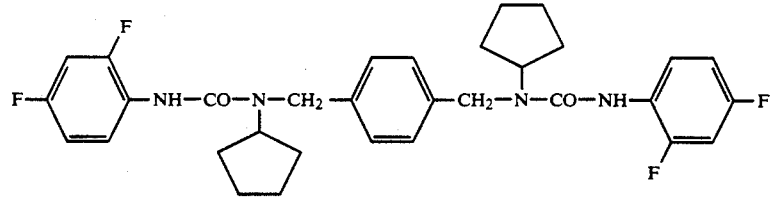

1,4-Bis[[1-cyclopentyl-3-(2,4-difluorophenyl)ureido]-methyl]benzene.

(i) M.p. 165°–167° C.
(ii) Mass (FAB) m/z 583 (M$^+$+1)

| (iii) Elemental analysis (C$_{32}$H$_{34}$N$_4$O$_2$F$_4$) | | | |
|---|---|---|---|
| | C | H | N |
| Calcd. (%) | 65.97 | 5.88 | 9.62 |
| Found (%) | 65.96 | 5.94 | 9.58 |

Example 16

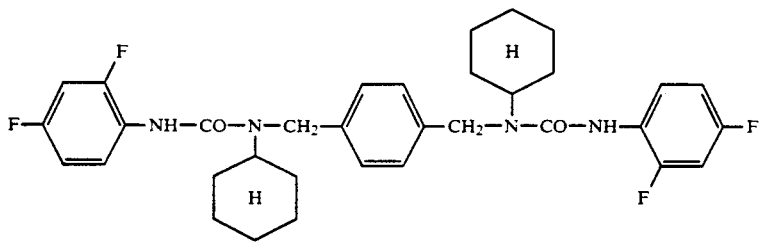

1,4-Bis[[1-cyclohexyl-3-(2,4-difluorophenyl)ureido]-methyl]benzene.

(i) M.p. 176°-177° C.
(ii) Mass (FAB) m/z 611 (M++1)

| (iii) Elemental analysis ($C_{34}H_{38}N_4O_2F_4$) | | | |
|---|---|---|---|
|  | C | H | N |
| Calcd. (%) | 66.87 | 6.27 | 9.17 |
| Found (%) | 66.69 | 6.28 | 9.08 |

-continued

| (iii) Elemental analysis ($C_{34}H_{38}N_4O_2F_4$) | | | |
|---|---|---|---|
|  | C | H | N |
| Found (%) | 66.99 | 6.21 | 8.96 |

Example 18

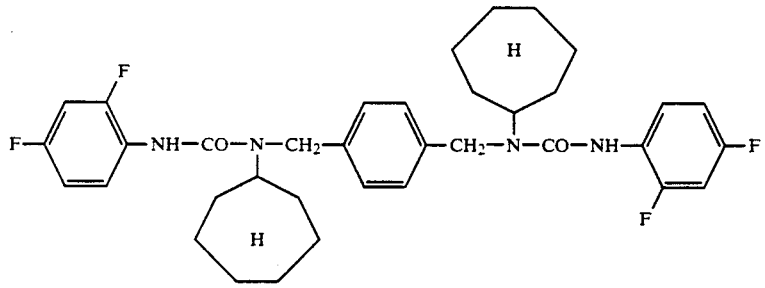

1,4-Bis[[1-cycloheptyl-3-(2,4-difluorophenyl)ureido]-methyl]benzene.

(i) M.p. 89°-91° C.
(ii) Mass (FAB) m/z 639 (M++1)

| (iii) Elemental analysis ($C_{36}H_{42}N_4O_2F_4$) | | | |
|---|---|---|---|
|  | C | H | N |
| Calcd. (%) | 67.69 | 6.63 | 8.77 |
| Found (%) | 67.62 | 6.81 | 8.62 |

Example 17

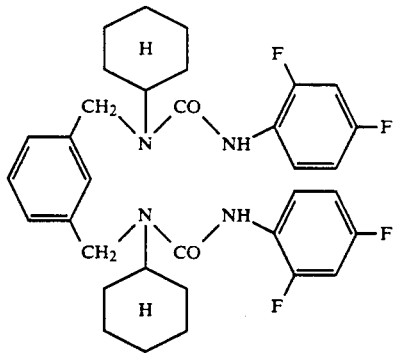

1,3-Bis[[1-cyclohexyl-3-(2,4-difluorophenyl)ureido]-methyl]benzene.

(i) M.p. 98°-99° C.
(ii) Mass (FAB) m/z 611 (M++1)

| (iii) Elemental analysis ($C_{34}H_{38}N_4O_2F_4$) | | | |
|---|---|---|---|
|  | C | H | N |
| Calcd. (%) | 66.87 | 6.27 | 9.17 |

Example 19

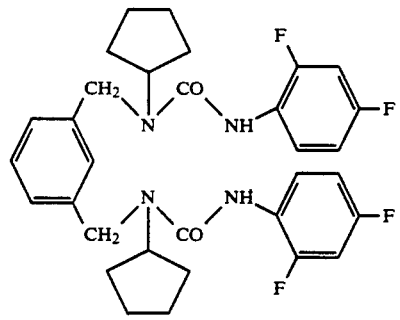

1,3-Bis[[1-cyclopentyl-3-(2,4-difluorophenyl)ureido]-methyl]benzene.

(i) M.p. 150°-151° C.
(ii) Mass (FAB) m/z 583 (M++1)

| (iii) Elemental analysis ($C_{32}H_{34}N_4O_2F_4$) | | | |
|---|---|---|---|
| | C | H | N |
| Calcd. (%) | 65.97 | 5.88 | 9.62 |
| Found (%) | 65.73 | 5.97 | 9.60 |

Example 20

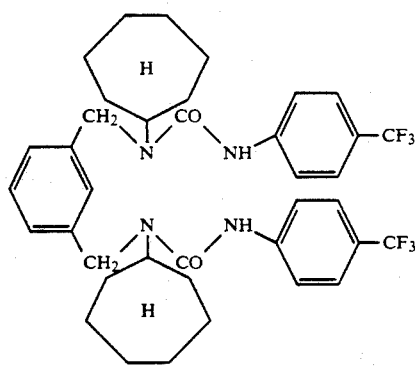

1,3-Bis[[1-cyclopentyl-3-(p-trifluoromethylphenyl)-ureido]methyl]benzene (i) M.p. 169°–170° C.
(ii) Mass (FAB) m/z 703 ($M^+ +1$)

| (iii) Elemental analysis ($C_{38}H_{44}N_4O_2F_6$) | | | |
|---|---|---|---|
| | C | H | N |
| Calcd. (%) | 64.94 | 6.31 | 7.97 |
| Found (%) | 64.89 | 6.35 | 7.94 |

Example 21

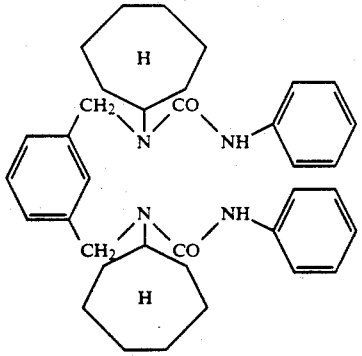

1,3-Bis[(1-cyclohexyl-3-phenylureido)methyl]benzene (i) M.p. 160°–162° C.
(ii) Mass (FAB) m/z 567 ($M^+ +1$)

| (iii) Elemental analysis ($C_{36}H_{46}N_4O_2$) | | | |
|---|---|---|---|
| | C | H | N |
| Calcd. (%) | 76.29 | 8.18 | 9.88 |
| Found (%) | 76.27 | 8.32 | 9.83 |

Example 22

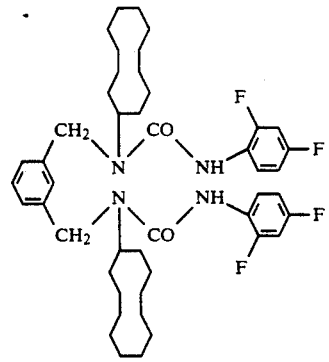

1,3-Bis[[1-cyclododecyl-3-(2,4-difluorophenyl)ureido]-methyl]benzene (i) M.p. 166°–167° C.
(ii) Mass (FAB) m/z 779 ($M^+ +1$)

| (iii) Elemental analysis ($C_{46}H_{62}N_4O_2F_4$) | | | |
|---|---|---|---|
| | C | H | N |
| Calcd. (%) | 70.92 | 8.02 | 7.19 |
| Found (%) | 71.01 | 8.16 | 7.05 |

Example 23

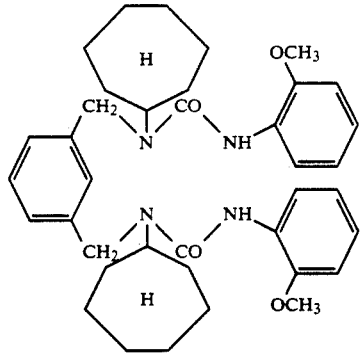

1,3-Bis[[1-cycloheptyl-3-(o-methoxyphenyl)ureido]-methyl]benzene (i) M.p. 160°–162° C.
(ii) Mass (FAB) m/z 627 ($M^+ +1$)

| (iii) Elemental analysis ($C_{38}H_{50}N_4O_4$) | | | |
|---|---|---|---|
| | C | H | N |
| Calcd. (%) | 72.81 | 8.04 | 8.94 |
| Found (%) | 72.78 | 8.07 | 8.90 |

Example 24

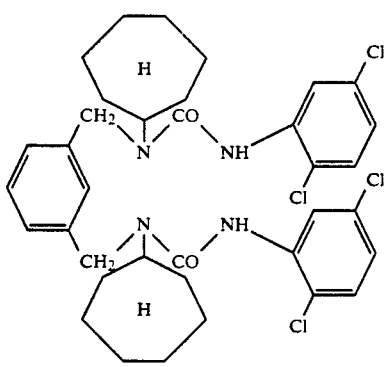

1,3-Bis[[1-cycloheptyl-3-(2,5-dichlorophenyl)ureido]-methyl]benzene (i) M.p. 153°–155° C.

(ii) Mass (FAB) m/z 705 (M$^+$ +1)

| (iii) Elemental analysis ($C_{36}H_{42}N_4O_2Cl_4$) | | | |
|---|---|---|---|
| | C | H | N |
| Calcd. (%) | 61.37 | 6.01 | 7.95 |
| Found (%) | 61.27 | 5.93 | 7.93 |

Example 24

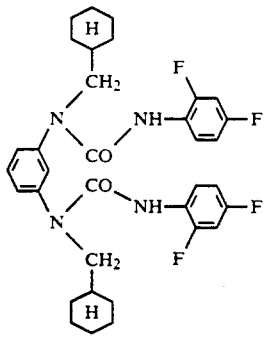

1,3-Bis[1-cyclohexylmethyl-3-(2,4-difluorophenyl)-ureido]benzene (i) M.p. 183°–185° C.

(ii) Mass (FAB) m/z 611 (M$^+$ +1)

| (iii) Elemental analysis ($C_{34}H_{38}N_4O_2F_4$) | | | |
|---|---|---|---|
| | C | H | N |
| Calcd. (%) | 66.87 | 6.27 | 9.17 |
| Found (%) | 66.72 | 6.40 | 9.09 |

Example 25

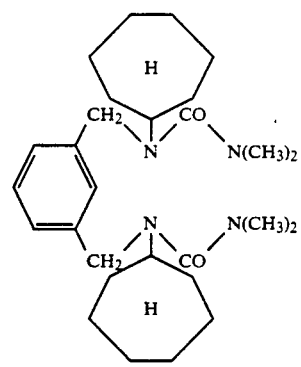

To a solution of 0.6 g N,N'-dicycloheptyl-m-xylylenediamine and 0.44 g triethylamine in 20 ml methylene dichloride, was added dropwise 5 ml of a methylene dichloride solution containing 0.47 g N,N-dimethylcarbamic chloride, and stirring was continued at room temperature for 12 hours. The reaction mixture was washed with water, dilute hydrochloric acid and water in that order, and dried over a drying agent. After distilling off the solvent, the residue was purified by silica gel column chromatography, giving 0.24 g of 1,3-bis[(1-cycloheptyl-3,3-dimethylureido)methyl]benzene as oil.

(i) $^1$H-NMR (CDCl$_3$, δ ppm) 2.80 (12H, s), 4.24 (4H, s)

(ii) Mass (FAB) m/z 471 (M$^+$ +1)

(iii) IR (cm$^{-1}$), 1654, 1492, 1460, 1174

Example 26

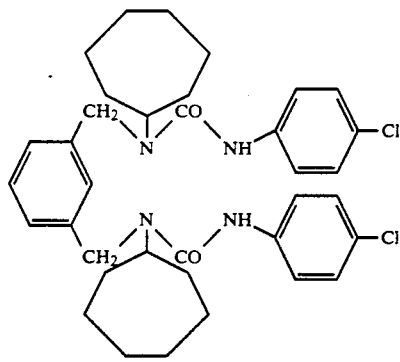

To a solution of 0.5 g N,N'-dicycloheptyl-m-xylylenediamine in 50 ml n-hexane, was added dropwise with stirring 5 ml of a n-hexane solution containing 0.25 g 4-chlorophenyl isocyanate under ice cooling, and stirring was continued at room temperature for two hours. After distilling off the solvent under reduced pressure, the residue was purified by silica gel column chromatography, giving 0.9 g of 1,3-bis[[3-(p-chlorophenyl)-1-cycloheptylureido]methyl]benzene as amorphous solid.

(i) $^1$H-NMR (CDCl$_3$, δ ppm) 1.20–2.20 (26H, m), 4.40 (4H, s), 1.12 (2H, s)

(ii) Mass (FAB) m/z 635 (M$^+$)

(iii) IR (cm$^{-1}$) 1646, 1526, 1496

The following two compounds were prepared in much the same manner as in Example 26.

Example 27

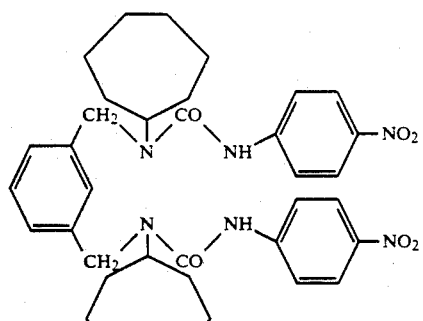

1,3-Bis[[1-cycloheptyl-3-(p-nitrophenyl)ureido]-methyl]benzene (i) $^1$H-NMR (CDCl$_3$, δ ppm) 4.52 (4H, s), 6.56 (2H, s), 8.04 (4H, d)
(ii) Mass (FAB) m/z 657 (M$^+$+1)
(iii) IR (cm$^{-1}$), 1674, 1542, 1504, 1334

Example 28

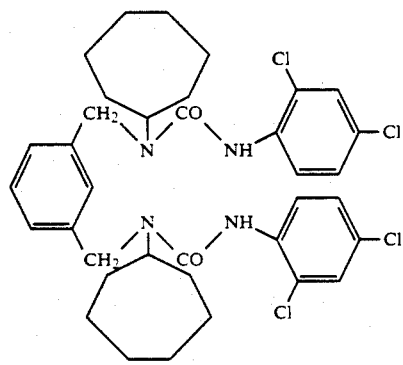

1,3-Bis[[1-cycloheptyl-3-(2,4-dichlorophenyl)ureido]-methyl]benzene (i) $^1$H-NMR (CDCl$_3$, δ ppm) 4.56 (4H, s), 6.75 (2H, s), 8.18 (2H, d)
(ii) Mass (FAB) m/z 765 (M$^+$+1)
(iii) IR (cm$^{-1}$), 1678, 1582, 1518, 1302

Example 29

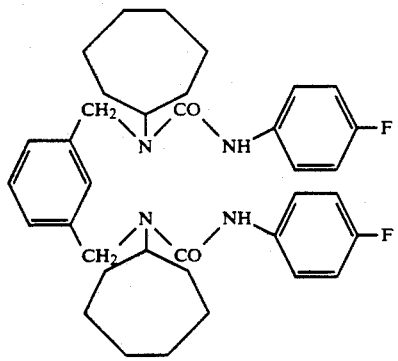

To a solution of 0.5 g N,N'-dicycloheptyl-m-xylylenediamine in 50 ml n-hexane, was added dropwise with stirring 5 ml of a n-hexane solution containing 0.46 g 4-fluorophenyl isocyanate under ice cooling, and stirring was continued at room temperature for two hours. The solid which separated out was collected by filtration, washed with n-hexane and recrystallized from methanol, giving 0.75 g of 1,3-bis[[1-cycloheptyl-3-(p-fluorophenyl)ureido]methyl]benzene.

(i) M.p. 183°–185° C.
(ii) Mass (FAB) m/z 603 (M$^+$+1)

|  | (iii) Elemental analysis (C$_{36}$H$_{44}$N$_4$O$_2$F$_2$) | | |
|---|---|---|---|
|  | C | H | N |
| Calcd. (%) | 71.74 | 7.36 | 9.29 |
| Found (%) | 71.70 | 7.37 | 9.29 |

The following seven compounds were prepared in much the same manner as in Example 29.

Example 30

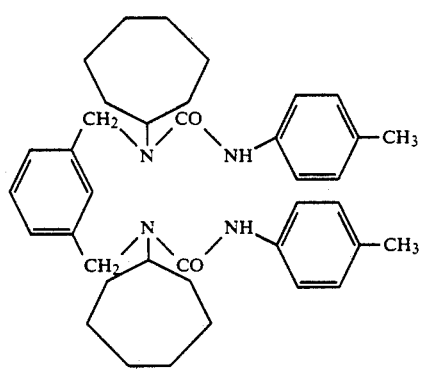

1,3-Bis[[1-cycloheptyl-3-(p-tolyl)ureido]-methyl]benzene (i) M.p. 147°–148° C.
(ii) Mass m/z 595 (M$^+$+1)

|  | (iii) Elemental analysis (C$_{38}$H$_{50}$N$_4$O$_2$) | | |
|---|---|---|---|
|  | C | H | N |
| Calcd. (%) | 76.73 | 8.47 | 9.42 |
| Found (%) | 76.65 | 8.54 | 9.27 |

Example 31

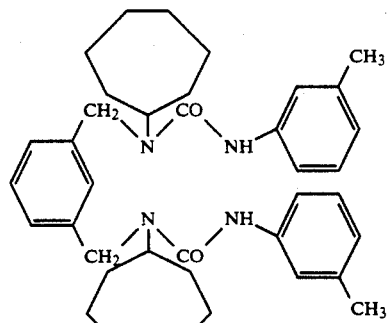

1,3-Bis[[1-cycloheptyl-3-(m-tolyl)ureido]-methyl]benzene (i) M.p. 171°–173° C.
(ii) Mass m/z 595 (M$^+$+1)

| (iii) Elemental analysis (C38H50N4O2) | | | |
|---|---|---|---|
|  | C | H | N |
| Calcd. (%) | 76.73 | 8.47 | 9.42 |
| Found (%) | 76.65 | 8.54 | 9.27 |

Example 32

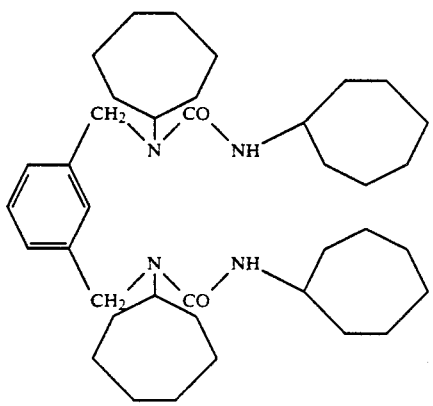

1,3-Bis[(1,3-dicycloheptylureido)methyl]benzene (i) M.p. 165°–167° C.
(ii) Mass m/z 607 (M+ +1)

| (iii) Elemental analysis (C38H62N4O2) | | | |
|---|---|---|---|
|  | C | H | N |
| Calcd. (%) | 75.20 | 10.30 | 9.23 |
| Found (%) | 74.90 | 10.44 | 8.95 |

Example 33

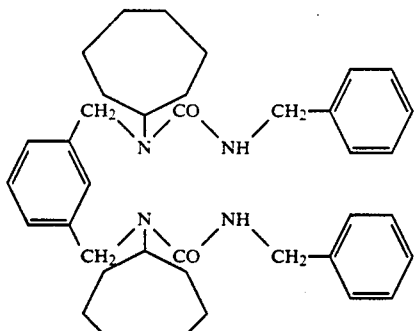

1,3-Bis[(3-benzyl-1-cycloheptylureido)-methyl]benzene (i) M.p. 173°–174° C.
(ii) Mass (FAB) m/z 595 (M+ +1)

| (iii) Elemental analysis (C38H50N4O2) | | | |
|---|---|---|---|
|  | C | H | N |
| Calcd. (%) | 76.73 | 8.47 | 9.42 |
| Found (%) | 76.74 | 8.52 | 9.35 |

Example 34

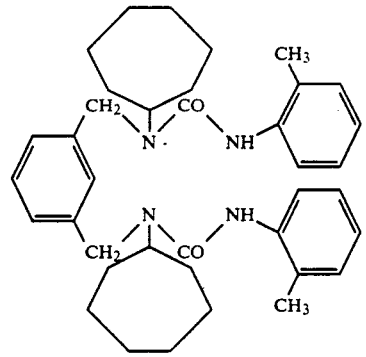

1,3-Bis[[1-cycloheptyl-3-(o-tolyl)ureido]-methyl]benzene (i) M.p. 183°–185° C.
(ii) Mass (FAB) m/z 595 (M+ +1)

| (iii) Elemental analysis | | | |
|---|---|---|---|
|  | C | H | N |
| Calcd. (%) | 76.73 | 8.47 | 9.42 |
| Found (%) | 76.67 | 8.50 | 9.33 |

Example 35

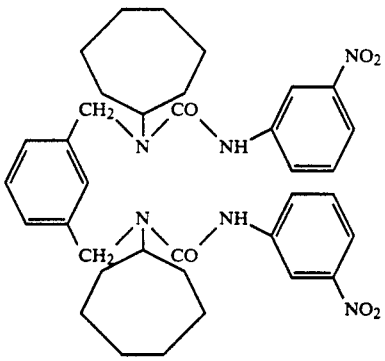

1,3-Bis[[1-cycloheptyl-3-(m-nitrophenyl)ureido]-methyl]benzene (i) M.p. 200°–201° C.
(ii) Mass (FAB) m/z 657 (M+ +1)

| (iii) Elemental analysis (C36H44N6O6) | | | |
|---|---|---|---|
|  | C | H | N |
| Calcd. (%) | 65.84 | 6.75 | 12.80 |
| Found (%) | 65.53 | 6.68 | 12.84 |

Example 36

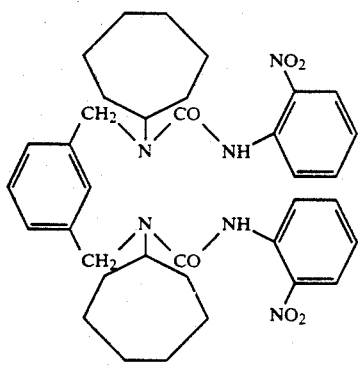

1,3-Bis[[1-cycloheptyl-3-(o-nitrophenyl)ureido]-methyl]benzene (i) M.p. 144°–145° C.
(ii) Mass (FAB) m/z 657 (M+ +1)

(iii) Elemental analysis ($C_{36}H_{44}N_6O_6$)

|  | C | H | N |
|---|---|---|---|
| Calcd. (%) | 65.84 | 6.75 | 12.80 |
| Found (%) | 65.63 | 6.71 | 12.86 |

Example 37

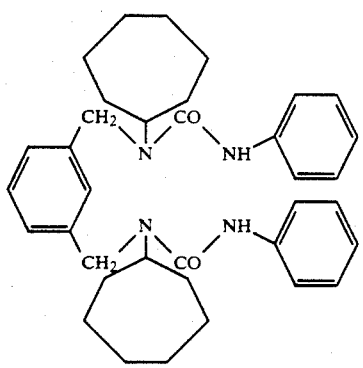

To a solution of 0.5 g N,N'-dicycloheptyl-m-xylylenediamine in 50 ml n-hexane, was added dropwise with stirring 5 ml of a n-hexane solution containing 0.45 g phenyl isothiocyanate under ice cooling, and stirring was continued at room temperature for two hours. The solid which separated out was collected by filtration, and recrystallized from methanol, giving 0.65 g of 1,3-bis[[1-cycloheptyl-3-phenyl(thioureido)]methyl]benzene.

(i) M.p. 146°–148° C.
(ii) Mass (FAB) m/z 599 (M+ +1)

(iii) Elemental analysis ($C_{36}H_{46}N_4S_2$)

|  | C | H | N |
|---|---|---|---|
| Calcd. (%) | 72.20 | 7.74 | 9.35 |
| Found (%) | 72.21 | 7.84 | 9.07 |

Example 38

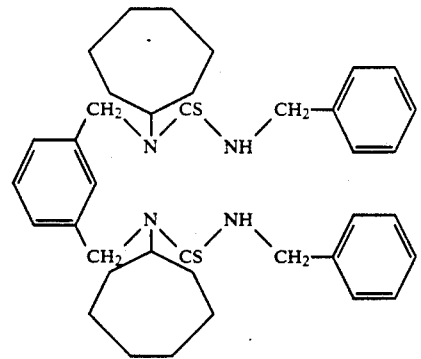

To a solution of 0.5 g N,N'-dicycloheptyl-m-xylylenediamine in 50 ml n-hexane, was added dropwise with stirring 5 ml of a n-hexane solution containing 0.5 g benzyl isothiocyanate under ice cooling, and stirring was continued at room temperature for 12 hours. After distilling off the solvent under reduced pressure, the residue was purified by silica gel column chromatography, giving 0.78 g of 1,3-bis[3-benzyl-1-cycloheptyl(thioureido)methyl]benzene as amorphous solid.

(i) $^1$H-NMR (CDCl$_3$, δppm) 4.56 (4H, s), 4.74 (4H, d)
(ii) Mass (FAB) m/z 627 (M+ +1)
(iii) IR (cm$^{-1}$), 1526, 1380, 1324

Example 39

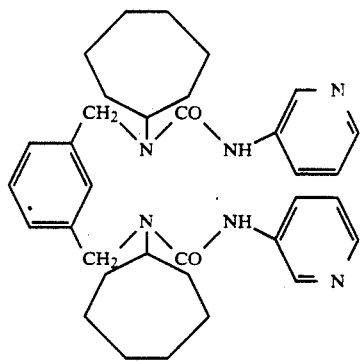

To a solution of 0.5 g N,N'-dicycloheptyl-m-xylylenediamine in 30 ml anhydrous toluene, was added 0.5 g β-pyridinecarboxylic azide, and the mixture was heated under reflux for one hour. After confirming the stop of gas evolution, the solvent was distilled off under reduced pressure, and the residue was purified by silica gel column chromatography and then recrystallized from diethyl ether, giving 0.5 g of 1,3-bis[[1-cycloheptyl-3-(3-pyridyl)ureido]methyl]benzene.

(i) M.p. 125°–127° C.
(ii) Mass (FAB) m/z 569 (M+ +1)

(iii) Elemental analysis ($C_{34}H_{44}N_6O_2$)

|  | C | H | N |
|---|---|---|---|
| Calcd. (%) | 71.80 | 7.80 | 14.78 |
| Found (%) | 71.97 | 7.76 | 14.65 |

The following three compounds were prepared in much the same manner as in Example 39.

Example 40

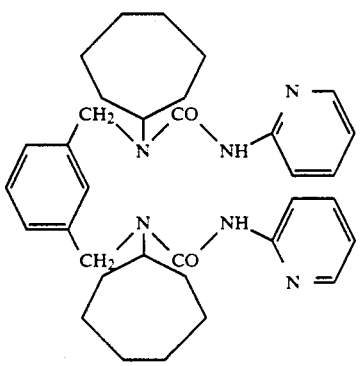

(i) ¹H-NMR (CDCl₃, δppm) 4.55 (4H, s), 7.56 (2H, dd), 7.65 (2H, dd)

(ii) Mass (FAB) m/z 569 (M⁺ +1)

(iii) IR (cm⁻¹), 1670, 1518, 1434, 1302

Example 41

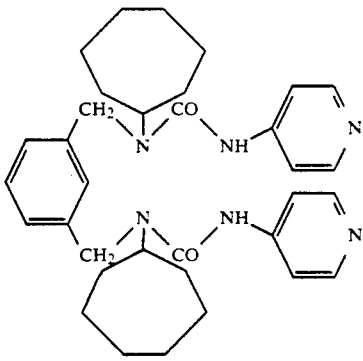

1,3-Bis[[1-cycloheptyl-3-(4-pyridyl)ureido]-methyl]benzene.

(i) M.p. 119°–121° C.

(ii) Mass (FAB) m/z 569 (M⁺ +1)

(iii) Elemental analysis (C₃₄H₄₄N₆O₂)

|  | C | H | N |
|---|---|---|---|
| Calcd. (%) | 71.80 | 7.80 | 14.78 |
| Found (%) | 71.68 | 7.77 | 14.87 |

Example 42

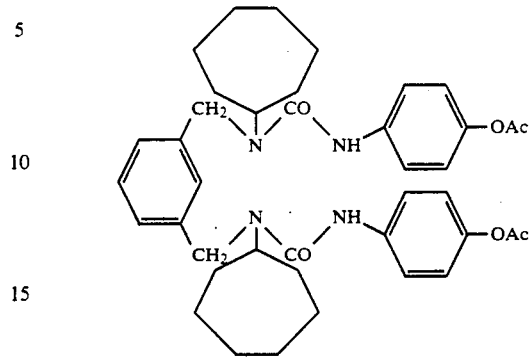

1,3-Bis[]3-(p-acetoxyphenyl)-1-cycloheptylureido]-methyl]benzene (i) ¹H-NMR (CDCl₃, δppm) 2.28 (6H, s), 4.50 (4H, s), 6.90 (4H, dd)

(ii) Mass (FAB) m/z 683 (M⁺ +1)

(iii) IR (cm⁻¹), 1766, 1652, 1532, 1510

Example 43

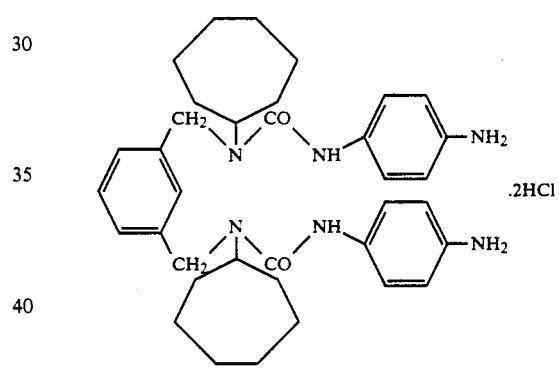

To a solution of 3 g 1,3-bis[[1-cycloheptyl-3-(p-nitrophenyl)ureido]methyl]benzene (compound of Example 28) in 50 ml N,N'-dimethylformamide, was added 300 ml of 10% Pd-carbon powder, and the mixture was subjected to catalytic hydrogenation. After a predetermined volume of hydrogen gas was absorbed, the catalyst was filtered off, the solvent was distilled off under reduced pressure from the filtrate, and the residue was purified by silica gel column chromatography, giving 1.5 g of 1,3-bis[[3-(p-aminophenyl)-1-cycloheptylureido]methyl]benzene as amorphous powder. This was treated with ethanolic hydrogen chloride, and the solid thus obtained was recrystallized from aqueous ethanol, affording 1.1 g of 1,3-bis[[1-cycloheptyl-3-(p-aminophenyl)ureido]methyl]benzene dihydrochloride.

(i) M.p. 228°–232° C. (dec.)

(ii) Mass (FAB) m/z 597 (M⁺ +1)

(iii) Elemental analysis (C₃₆H₅₀N₆O₂Cl₂)

|  | C | H | N |
|---|---|---|---|
| Calcd. (%) | 64.56 | 7.52 | 12.55 |
| Found (%) | 64.28 | 7.53 | 12.48 |

The following two compounds were prepared in much the same manner as in Example 43.

Example 44

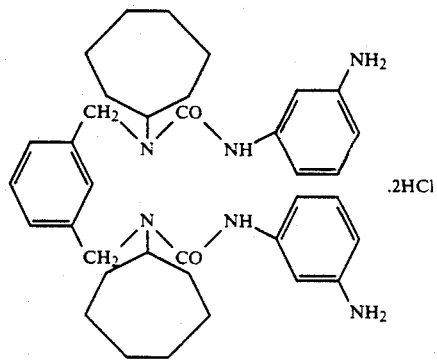

1,3-Bis[[3-(m-aminophenyl)-1-cycloheptylureido]-methyl]benzene dihydrochloride (i) $^1$H-NMR (DMSO-d$_6$, δppm) 4.56 (4H, s), 8.60 (2H, s)

(ii) Mass (FAB) m/z 597 (M$^+$ +1)

(iii) IR (cm$^{-1}$), 1642, 1610, 1542, 1496

Example 45

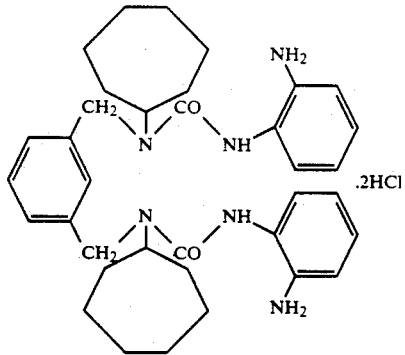

1,3-Bis[[3-(o-aminophenyl)-1-cycloheptylureido]-methyl]benzene dihydrochloride (i) $^1$H-NMR (DMSO-d$_6$, δppm) 4.56 (4H, s), 8.65 (2H, s)

(ii) Mass (FAB) m/z 597 (M$^+$ +1)

(iii) IR (cm$^{-1}$), 1636, 1522, 1458

Example 46

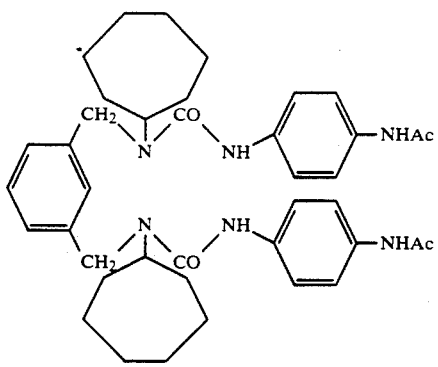

To a solution of 0.29 g 1,3-bis[[3-(p-aminophenyl)-1-cycloheptylureido]methyl]benzene (compound of Example 43) and 0.12 g triethylamine in 30 ml dichloromethane, was added dropwise with stirring 5 ml of a dichloromethane solution containing 92 mg acetyl chloride under ice cooling, and stirring was continued at room temperature for two hours. The reaction mixture was washed with dilute hydrochloric acid and water in that order, the solvent was distilled off under reduced pressure, and the residue was purified by silica gel column chromatography, giving 150 mg of 1,3-bis[[3-(p-acetamidophenyl)-1-cycloheptylureido]methyl]benzene as amorphous solid.

(i) $^1$H-NMR (CDCl$_3$, δppm) 2.10 (6H, s), 4.08 (4H, s), 7.00 (4H, d)

(ii) Mass (FAB) m/z 681 (M$^+$ +1)

(iii) IR (cm$^{-1}$), 1666, 1650, 1614, 1556

Example 47

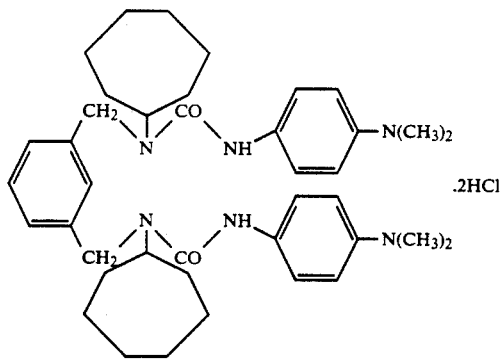

To a solution of 0.47 g 1,3-bis[[3-(p-aminophenyl)-1-cycloheptylureido]methyl]benzene (compound of Example 43) and 0.31 g of 37% formaline in 20 ml ethanol, was added 50 ml of platinum oxide, and the mixture was subjected to catalytic hydrogenation. After a predetermined volume of hydrogen gas was absorbed, the catalyst was filtered off, the solvents were distilled off under reduced pressure from the filtrate, and the residue was purified by silica gel column chromatography, giving 0.37 g of 1,3-bis[[1-cycloheptyl-3-(p-dimethylaminophenyl)ureido]methyl]benzene as amorphous powder. This was treated with ethanolic hydrogen chloride, and the solid thus obtained was recrystallized from ethanol, affording 0.25 g of 1,3-bis[[1-cycloheptyl-3-(p-dimethylaminophenyl)ureido]methyl]benzene dihydrochloride.

(i) M.p. 168°–170° C.
(ii) Mass (FAB) m/z 653 (M⁺+1)

| (iii) Elemental analysis ($C_{40}H_{58}N_6O_2Cl_2$) | | | |
|---|---|---|---|
| | C | H | N |
| Calcd. (%) | 66.19 | 8.05 | 11.58 |
| Found (%) | 66.21 | 7.87 | 11.41 |

Example 48

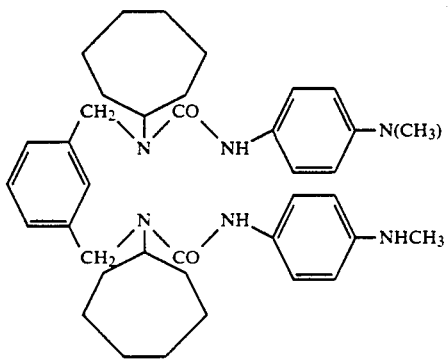

To a solution of 1 g 1,3-bis[[3-(p-aminophenyl)-1-cycloheptylureido]methyl]benzene (compound of Example 43) and 0.29 g of 35% formaline in 50 ml ethanol, was added 100 ml of platinum oxide, and the mixture was subjected to catalytic hydrogenation. After the absorption of hydrogen gas ceased, the catalyst was filtered off, the solvents were distilled off under reduced pressure from the filtrate, and the residue was purified by silica gel column chromatography, giving 0.19 g of 1-[[1-cycloheptyl-3-(p-dimethylaminophenyl)ureido]methyl]-3-[[1-cycloheptyl-3-(p-methylaminophenyl)ureido]methyl]benzene as amorphous powder.

(i) ¹H-NMR (CDCl₃, δ ppm) 2.74 (3H, s), 2.84 (6H, s), 4.46 (4H, s)
(ii) Mass (FAB) m/z 638 (M⁺)
(iii) IR (cm⁻¹), 1648, 1520, 1320, 1240

The following two compounds were prepared in much the same manner as in Example 48.

Example 49

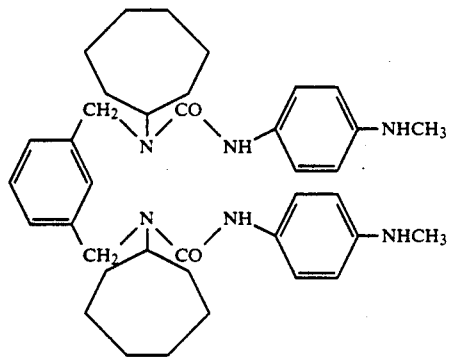

1,3-Bis[υ1-cycloheptyl-3-(p-methylaminophenyl)ureido]methyl]benzene 1,3-Bis[[1-cycloheptyl-3-(p-methylaminophenyl)ureido]-methyl]benzene (i) ¹H-NMR (CDCl₃, δ ppm) 2.76 (6H, s), 4.46 (4H, s), 6.46 (4H, d)
(ii) Mass (FAB) m/z 624 (M⁺)
(iii) IR (cm⁻¹), 1648, 1522, 1488, 1464

Example 50

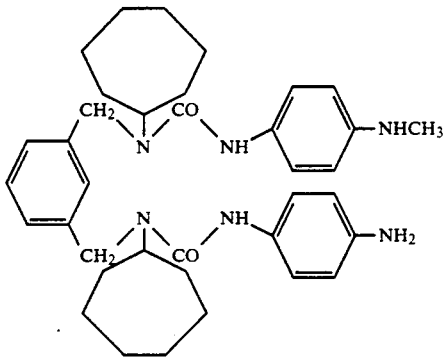

(i) ¹H-NMR (CDCl₃, δ ppm) 2.76 (3H, s), 4.48 (4H, s), 5.92 (2H, s)
(ii) Mass (FAB) 610 (M⁺)
(iii) IR (cm⁻¹), 1648, 1520, 1238

Example 51

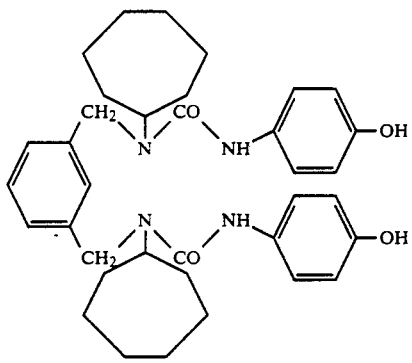

A mixture of 2 g 1,3-bis[[3-(p-acetoxyphenyl)-1-cycloheptylureido]methyl]benzene (compound of Example 42), 30 ml ethanol and 30 ml of 5% aqueous sodium carbonate solution was heated under reflux for ten minutes. After distilling off the ethanol under reduced pressure, water was added to the residue, and the resulting mixture was acidified by addition of concentrated hydrochloric acid under ice cooling. The solid which separated out was collected by filtration and recrystallized from methanol, giving 1 g of 1,3-bis[[1-cycloheptyl-3-(p-hydroxyphenyl)ureido]methyl]benzene.

(i) M.p. 230°–231° C.
(ii) Mass (FAB) m/z 599 (M⁺+1)

| (iii) Elemental analysis ($C_{36}H_{46}N_4O_4$) | | | |
|---|---|---|---|
| | C | H | N |
| Calcd. (%) | 72.21 | 7.74 | 9.36 |
| Found (%) | 72.18 | 7.72 | 9.23 |

Example 52

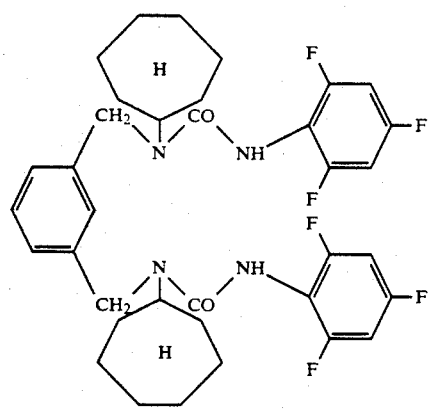

A mixture of 0.82 g N,N'-dicycloheptyl-m-xylylenediamine, 1.26 g phenyl 2,4,6-trifluorophenylcarbamate and 50 ml toluene was heated under reflux for one hour. After cooling, the reaction mixture was washed twice with 50 ml of 1N-NaOH solution and then with sodium chloride solution, and dried over anhydrous magnesium sulfate. The solvent was distilled off under reduced pressure from the dried solution, and the residue was recrystallized from acetone, giving 1.02 g of 1,3-bis[[1-cycloheptyl-3-(2,4,6-trifluorophenyl)ureido]methyl]benzene.

(i) M.p. 107°–108° C. (ii) Mass (FAB) m/z 674 (M+)

| (iii) Elemental analysis ($C_{36}H_{40}N_4F_6O_2$) | | | |
|---|---|---|---|
| | C | H | N |
| Calcd. (%) | 64.08 | 5.98 | 8.30 |
| Found (%) | 63.88 | 5.95 | 8.29 |

The following compound was prepared in much the same manner as in Example 27.

Example 53

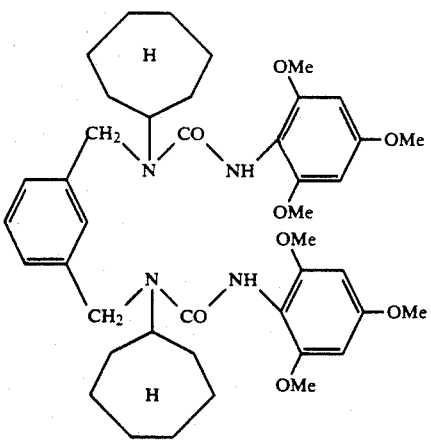

1,3-Bis[[3-(2,4,6-trimethoxyphenyl)-1-cycloheptylureido]-methyl]benzene
 (i) M.p. 133°–134.5° C.
 (ii) Mass (FAB) m/z 747 (M+)

| (iii) Elemental analysis ($C_{42}H_{58}N_4O_8$) | | | |
|---|---|---|---|
| | C | H | N |
| Calcd. (%) | 67.54 | 7.83 | 7.50 |
| Found (%) | 67.07 | 7.84 | 7.33 |

Example 54

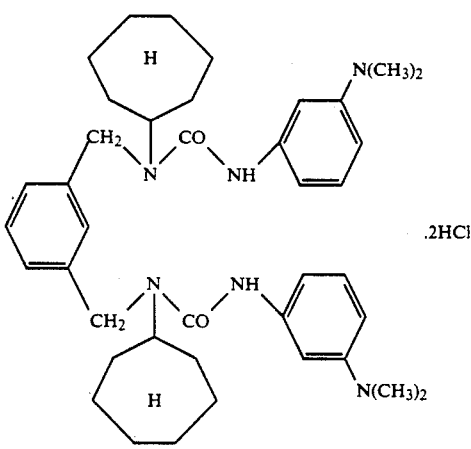

To a mixture of 0.50 g 1,3-bis[[3-(m-aminophenyl)-1-cycloheptylureido]methyl]benzene (compound of Example 44), 0.17 ml of 35% formaline, 30 ml acetonitrile and 100 ml chloroform, was added with stirring 0.11 g sodium cyanoborohydride at room temperature, and stirring was continued for 20 hours. Sodium cyanoborohydride (0.11 g) and 35% formaline (0.17 ml) were further added, and the mixture was stirred for two hours. Acetic acid (1 ml) was then added, and stirring was continued for an additional 30 minutes. The resulting solution was washed with 50 ml of 1N-KOH solution, the aqueous layer was extracted thrice with 100 ml chloroform, and the combined organic solution washed with aqueous solution of sodium chloride and dried over anhydrous sodium sulfate. The solvents were distilled off under reduced pressure from the dried solution, and the residue was purified by silica gel column chromatography, followed by treatment with ethanolic hydrogen chloride. Distilling off the solvent gave 0.25 g of 1,3-bis[[1-cycloheptyl-3-(m-dimethylaminophenyl)ureido]methyl]benzene dihydrochloride as amorphous powder.

(i) $^1$H-NMR (DMSO-$d_6$, δ ppm) 3.13 (12H, s), 4.59 (4H, s)

(ii) Mass (FAB) 653 (M+ + 1)

(iii) IR (cm$^{-1}$), 2936, 1654, 1540, 1464

Example 55

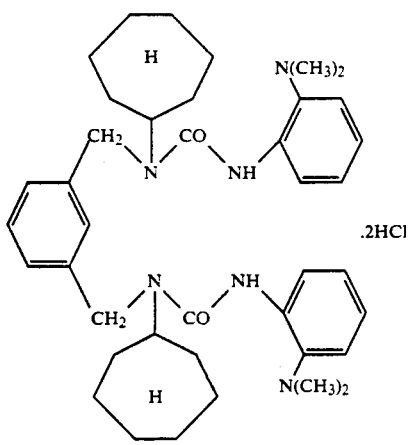

.2HCl

To a mixture of 0.6 g 1,3-bis[[3-(o-aminophenyl)1-cycloheptylureido]methyl]benzene (compound of Example 45), 0.43 ml of 35% formaline, 50 ml acetonitrile and 50 ml benzene, was added with stirring 0.12 g sodium cyanoborohydride at room temperature, and stirring was continued for two hours. Sodium cyanoborohydride (0.12 g) and 35 formaline (0.43 ml) were further added, and the mixture was stirred for two hours. Acetic acid (1 ml) was then added, and stirring was continued for an additional 30 minutes. The solvents were distilled off from the reaction mixture, and 50 ml of 1N-KOH solution was added, followed by extraction with 50 ml chloroform three times. The extract was washed with saturated aqueous solution of sodium chloride was dried over anhydrous potassium carbonate. The solvent was distilled off under reduced pressure from the dried solution, and the residue was purified by silica gel column chromatography and then recrystallized from acetone, giving 0.16 g of 1,3-bis[[1-cycloheptyl-3-(o-dimethylaminophenyl)ureido]methyl]benzene dihydrochloride.

(i) M.p. 159°-160° C.
(ii) Mass (FAB) m/z 653 (M+)

| (iii) Elemental analysis ($C_{40}H_{56}N_6O_2$) | | | |
|---|---|---|---|
| | C | H | N |
| Calcd. (%) | 73.58 | 8.64 | 12.87 |
| Found (%) | 73.42 | 8.75 | 12.76 |

Example A

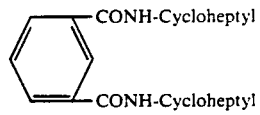

20.8 g of cycloheptylamine and 20.25 g of triethylamine were dissolved in 500 ml of methylenechloride, and then, 17.0 g of iso-phthaloyl chloride was added to thereto. The mixture was stirred at room temperature for 2 hours, and 500 ml of water was added to the reaction mixture. Then, conc. HCl was added thereto while stirring. Precipitated soli material was collected by filtration, washed with methylene chloride and water successively, and dried giving 28.7 g of N,N'-dicycloheptylisophthalamide.

mp. 285°-286° C.
IR (cm$^{-1}$): 3264, 1648, 1632, 1560
Mass (m/z): 356 (M+)

Example B

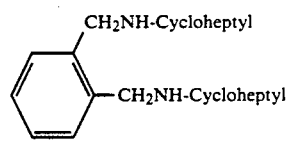

24.3 g of N,N'-dicycloheptylisophthalamide (obtained in the above Example B) was suspended in 500 ml of toluene, and 96 ml of toluene solution (70%) containing bis(2-methoxyethoxy) aluminum sodium hydride was added thereto dropwise while stirring at room temperature. The mixture was refluxed under heating for 3 hours, and 400 ml of 2.5N sodium hydroxyde aqueous solution was added thereto portionwise. The toluene layer was separated and collected. The collected toluene solution was washed with saturated aqueous NaCl solution, and dried. The solution was removed by distillation, giving 22.3 g of N,N-dicycloheptyl-m-xylenediamine.

$^1$H-NMR (CDCl$_3$, δ, ppm): 3.74 (4H, s), 7.08-7.36 (4H, m),
IR (cm$^{-1}$): 2936, 2860, 1462, 1114
Mass (FAB) m/z 329 (M$^+$+1)

Example 56

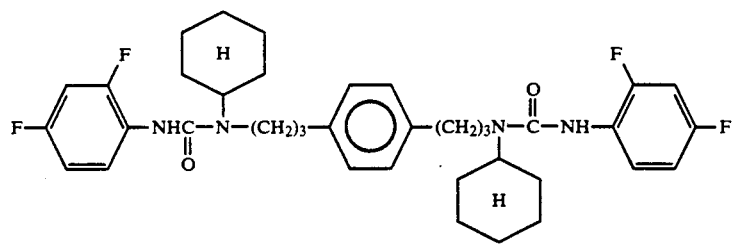

The above compound was prepared in much the same manner as in Example 13.

(i) M.p. 76°-78° C.
(ii) $^1$H-NMR (CDCl$_3$, δ ppm) 2.14 (4H, t), 3.20 (4H, t), 6.26 (2H, d) (iii) Elemental analysis ($C_{38}H_{46}N_4O_2F_4$)

| (iii) Elemental analysis (C₃₈H₄₆N₄O₂F₄) | | | |
|---|---|---|---|
| | C | H | N |
| Calcd. (%) | 68.45 | 6.95 | 8.40 |
| Found (%) | 68.66 | 7.13 | 8.22 |

Example 57

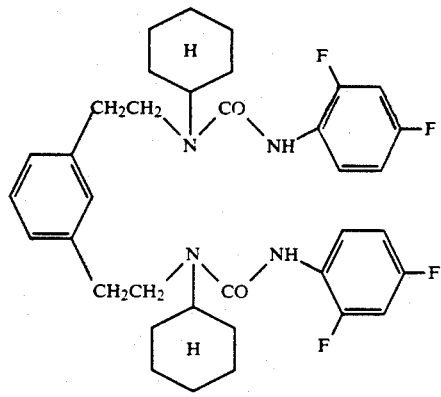

The above compound was prepared in much the same manner as in Example 1.
(i) ¹H-NMR (CDCl₃, δ ppm) 2.88 (4H, t), 3.32 (4H, t), 6.38 (2H, d)
(ii) IR (cm⁻¹) 2944, 1654, 1522, 1432

Example C

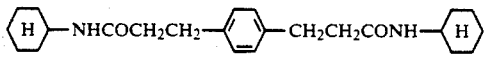

To a solution of 4.9 g of cyclohexylamine and 5.4 g of triethylamine in 100 ml of methylenechloride, was added 5.8 g of 1,4-phenylenedipropionyl chloride under ice cooling with stirring. Stirring was continued for 3 hours at room temperature, and 500 ml of water was added to the reaction solution. Conc.-HCl was added to the mixture until aqueous layer became weak-acidic. The solid material precipitated was collected by filtration, washed with methylenechloride and water in that order, and dried, giving 7.4 g of N,N'-dicyclohexyl-1,4-phenylenedipropionamide.
(i) M.p. 267°–269° C.
(ii) IR (cm⁻¹) 3312, 1642, 1548

Example D

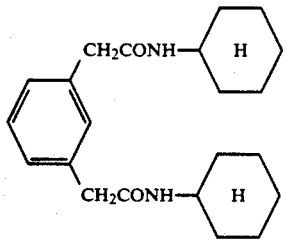

N,N-dicyclohexyl-1,3-phenylenediacetamide (i) M.p. 221°–222° C.
(ii) IR (cm⁻¹) 3304, 2944, 1646, 1550

Example E

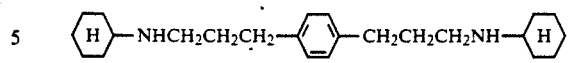

1.5 g of N,N'-dicyclohexyl-1,4-phenylenedipropionamide was added to 20 ml of dry tetrahydrofuran, and after adding thereto dropwise 2.4 ml of borandimethyl sulfide complex under ice cooling, the mixture was refluxed under heating for 4 hours. After adding to the mixture 0.33 ml of methanol under ice cooling and stirring the mixture for 30 minutes at room temperature, 2 ml of conc.-HCl was added to the mixture under ice cooling. The mixture was refluxed under heating for 30 minutes. The reaction solution was ice-cooled, and the solid material precipitated was collected by filtration, and washed with ether. The sold material thus obtained was dissolved in chloroform, and the solution was alkalified with aqueous NaOH solution. The chloroform layer was dried, and the solvent was distilled away under reduced pressure, giving 1.3 g of N,N'-dicyclohexyl-1,4-phenylenedipropylamine.
(i) ¹H-NMR (CDCl₃, δ ppm) 7.12 (4H, s)
(ii) IR (cm⁻¹) 2936, 2856, 1516, 1452
(iii) Mass spectrum (EI) m/z 356 (M+)

Example F

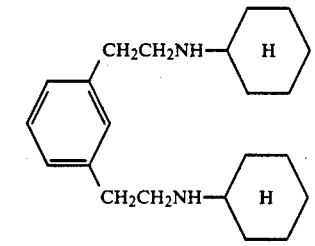

N,N-dicyclohexyl-1,3-phenylenediethylamine

The above compound was prepared in much the same manner as in Example E.
(i) ¹H-NMR (CDCl₃, δ ppm) 2.90 (8H, t)
(ii) IR (cm⁻¹) 2936, 2856, 1452, 1130

We claim:
1. A compound of the formula (I):

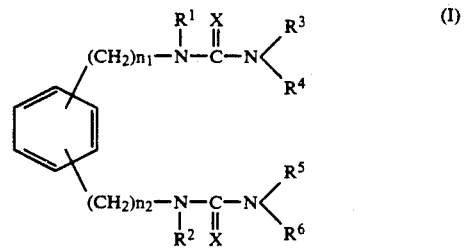

wherein $R^1$ and $R^2$, which are the same or different, each represents an alkyl group ($C_1$-$C_{10}$), a cycloalkyl group ($C_3$-$C_{18}$) or a lower alkyl group ($C_1$-$C_5$) substituted by a cycloalkyl group ($C_3$-$C_{18}$); $R^3$, $R^4$, $R^5$ and $R^6$, which are the same or different, each represents a hydrogen atom, a lower alkyl group ($C_1$-$C_5$), a cycloalkyl group ($C_3$-$C_{18}$), pyridyl, pyridylalkyl, or a phenyl group which is unsubstituted or substituted by at least one group selected from lower alkyl ($C_1$–$C_5$), halogeno-lower-alkyl, halogen, nitro, amino, mono or di-lower alkylamino, lower acylamino ($C_1$–$C_5$) hydroxyl, lower alkoxy or lower acyloxy ($C_2$–$C_5$); and wherein at least one of $R^3$–$R^6$ represents a pyridyl group or a pyridylalkyl group wherein said alkyl is ($C_1$–$C_{10}$); X represents a sulfur atom; and $n_1$ and $n_2$, which are the same or different, each represents an integer of from 1 to 6; or a salt of the formula (I) compound.

2. The compound of claim 1 wherein $R^1$ and $R^2$ are cycloalkyl groups ($C_3$–$C_{18}$); $R^3$ and $R^5$ are hydrogen; $R^4$ and $R^6$ are pyridyl; and $n_1$ and $n_2$ are 1.

3. The compound of claim 1 wherein $R^1$ and $R^2$ are cycloalkyl groups ($C_3$–$C_{18}$); $R^3$ and $R^5$ are hydrogen; $R^4$ and $R^5$ are pyridylalkyl wherein said alkyl is ($C_1$–$C_{10}$); and $n_1$, and $n_2$ are 1.

4. The compound of claim 1 which is 1,3-[[1-cycloheptyl-3-(3-pyridyl)ureido]-methyl]benzene.

5. The compound of claim 1 which is 1,3-bis[[1-cycloheptyl3-(2-pyridyl)ureido]-methyl]benzene.

6. The compound of claim 1 which is 1,3-bis[[1-cycloheptyl3-(4-pyridyl)ureido]-methyl]benzene.

* * * * *